United States Patent
Burkholz et al.

(10) Patent No.: US 10,549,072 B2
(45) Date of Patent: Feb. 4, 2020

(54) INTEGRATED CATHETER WITH INDEPENDENT FLUID PATHS

(71) Applicant: Becton, Dickinson and Company, Franklin Lakes, NJ (US)

(72) Inventors: Jonathan Karl Burkholz, Salt Lake City, UT (US); Bin Wang, Sandy, UT (US); Bart D. Peterson, Farmington, UT (US); Ralph L. Sonderegger, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 304 days.

(21) Appl. No.: 15/286,162

(22) Filed: Oct. 5, 2016

(65) Prior Publication Data

US 2017/0120010 A1     May 4, 2017

Related U.S. Application Data

(60) Provisional application No. 62/247,596, filed on Oct. 28, 2015, provisional application No. 62/296,383, (Continued)

(51) Int. Cl.
*A61M 25/06* (2006.01)
*A61M 5/158* (2006.01)
*A61M 5/162* (2006.01)

(52) U.S. Cl.
CPC ........ *A61M 25/0606* (2013.01); *A61M 5/158* (2013.01); *A61M 5/1626* (2013.01); (Continued)

(58) Field of Classification Search
CPC ............... A61M 25/06; A61M 5/1626; A61M 25/0097; A61M 25/0631
(Continued)

(56) References Cited

U.S. PATENT DOCUMENTS 3,046,984 A   7/1962 Eby
3,547,119 A   12/1970 Hall et al.
(Continued)

FOREIGN PATENT DOCUMENTS

CA     2 133 053 A1    3/1995
CN     101879341 A     11/2010
(Continued)

OTHER PUBLICATIONS

Silva, Elson, Email Regarding "Respecting Hydrology Science and IP Rights—US Pat. Application 20110130728," pp. 1-6 (Jun. 2, 2011).

*Primary Examiner* — Phillip A Gray
(74) *Attorney, Agent, or Firm* — Kirton & McConkie; Craig Metcalf; Kevin Stinger

(57) ABSTRACT

Catheter systems comprising independent fluid paths are disclosed. The catheter systems can include a catheter adapter that has a catheter hub with a chamber. A catheter extends from a distal end of the catheter hub and is in fluid communication with the chamber. A stabilization platform with a first wing and a soft push tab are also part of the catheter hub. The catheter system includes a needle hub with a needle that slidably fits within the catheter. In an insertion configuration, a proximal extension of the catheter hub is removably coupled within a distal opening of the needle hub. After the catheter is placed, the needle hub is retracted from the catheter adapter to slidably remove the needle from the catheter.

14 Claims, 11 Drawing Sheets

Related U.S. Application Data filed on Feb. 17, 2016, provisional application No. 62/247,599, filed on Oct. 28, 2015, provisional application No. 62/247,617, filed on Oct. 28, 2015, provisional application No. 62/247,607, filed on Oct. 28, 2015, provisional application No. 62/247,621, filed on Oct. 28, 2015, provisional application No. 62/247,624, filed on Oct. 28, 2015, provisional application No. 62/247,626, filed on Oct. 28, 2015, provisional application No. 62/296,385, filed on Feb. 17, 2016.

(52) U.S. Cl.
CPC .... *A61M 25/0631* (2013.01); *A61M 25/0693* (2013.01); *A61M 25/0637* (2013.01); *A61M 2205/586* (2013.01)

(58) Field of Classification Search
USPC ........................................................ 604/510
See application file for complete search history.

(56) References Cited

U.S. PATENT DOCUMENTS

| | | |
|---|---|---|
| 3,589,361 A | 6/1971 | Loper et al. |
| 3,827,434 A | 8/1974 | Thompson et al. |
| 3,853,127 A | 12/1974 | Spademan |
| 3,859,998 A | 1/1975 | Thomas et al. |
| 4,003,403 A | 1/1977 | Nehring |
| 4,043,346 A | 8/1977 | Mobley et al. |
| 4,099,528 A | 7/1978 | Sorenson et al. |
| 4,149,539 A | 4/1979 | Cianci |
| 4,172,448 A | 10/1979 | Brush |
| 4,177,809 A | 12/1979 | Moorehead |
| 4,193,399 A | 3/1980 | Robinson |
| 4,200,096 A | 4/1980 | Charvin |
| 4,269,186 A | 5/1981 | Loveless et al. |
| 4,311,137 A | 1/1982 | Gerard |
| 4,317,445 A | 3/1982 | Robinson |
| 4,326,519 A | 4/1982 | D'Alo et al. |
| 4,353,369 A | 10/1982 | Muetterties et al. |
| 4,362,156 A | 12/1982 | Feller, Jr. et al. |
| 4,365,630 A | 12/1982 | McFarlane |
| 4,387,879 A | 6/1983 | Tauschinski |
| 4,419,094 A | 12/1983 | Patel |
| 4,445,893 A | 5/1984 | Bodicky |
| 4,449,693 A | 5/1984 | Gereg |
| 4,496,348 A | 1/1985 | Genese et al. |
| 4,525,157 A | 6/1985 | Vaillancourt |
| 4,531,935 A | 7/1985 | Berryessa |
| 4,682,980 A | 7/1987 | Suzuki |
| 4,701,162 A | 10/1987 | Rosenberg |
| 4,703,761 A | 11/1987 | Rathbone et al. |
| 4,758,225 A | 7/1988 | Cox et al. |
| 4,765,588 A | 8/1988 | Atkinson |
| 4,772,264 A | 9/1988 | Cragg |
| 4,813,939 A | 3/1989 | Marcus |
| 4,834,708 A | 5/1989 | Pillari |
| 4,842,591 A | 6/1989 | Luther |
| 4,874,377 A | 10/1989 | Newgard et al. |
| 4,894,052 A | 1/1990 | Crawford |
| 4,917,668 A | 4/1990 | Haindl |
| 4,917,671 A | 4/1990 | Chang |
| 4,925,444 A | 5/1990 | Orkin et al. |
| 4,935,010 A | 6/1990 | Cox et al. |
| 4,950,257 A | 8/1990 | Hibbs et al. |
| 4,966,586 A | 10/1990 | Vaillancourt |
| D315,822 S | 3/1991 | Ryan |
| 5,032,116 A | 7/1991 | Peterson et al. |
| 5,041,097 A | 8/1991 | Johnson |
| 5,053,014 A | 10/1991 | Van Heugten |
| 5,057,087 A | 10/1991 | Harmon |
| 5,059,186 A | 10/1991 | Yamamoto et al. |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,135,504 A | 8/1992 | McLees |
| 5,154,703 A | 10/1992 | Bonaldo |
| 5,156,596 A | 10/1992 | Balbierz et al. |
| 5,176,653 A | 1/1993 | Metals |
| 5,176,662 A | 1/1993 | Bartholomew et al. |
| 5,201,717 A | 4/1993 | Wyatt et al. |
| 5,211,634 A | 5/1993 | Vaillancourt |
| 5,215,525 A | 6/1993 | Sturman |
| 5,215,528 A | 6/1993 | Purdy et al. |
| 5,215,529 A | 6/1993 | Fields et al. |
| 5,226,883 A | 7/1993 | Katsaros et al. |
| 5,234,410 A | 8/1993 | Graham et al. |
| 5,242,411 A | 9/1993 | Yamamoto et al. |
| 5,254,097 A | 10/1993 | Schock et al. |
| 5,267,971 A | 12/1993 | Brimhall |
| 5,269,764 A | 12/1993 | Vetter et al. |
| 5,273,546 A | 12/1993 | McLaughlin et al. |
| 5,290,222 A | 3/1994 | Feng et al. |
| 5,290,246 A | 3/1994 | Yamamoto et al. |
| 5,295,969 A | 3/1994 | Fischell et al. |
| 5,306,243 A | 4/1994 | Bonaldo |
| 5,312,359 A | 5/1994 | Wallace |
| 5,328,482 A | 7/1994 | Sircom et al. |
| 5,330,435 A | 7/1994 | Vaillancourt |
| 5,342,315 A | 8/1994 | Rowe et al. |
| 5,350,363 A | 9/1994 | Goode et al. |
| 5,352,205 A | 10/1994 | Dales et al. |
| 5,356,381 A | 10/1994 | Ensminger et al. |
| 5,368,029 A | 11/1994 | Holcombe et al. |
| 5,405,323 A | 4/1995 | Rogers et al. |
| 5,447,501 A | 9/1995 | Karlsson et al. |
| 5,456,675 A | 10/1995 | Wolbring et al. |
| 5,458,658 A | 10/1995 | Sircom |
| 5,487,728 A | 1/1996 | Vaillancourt |
| 5,498,241 A | 3/1996 | Fabozzi |
| 5,509,912 A | 4/1996 | Vaillancourt et al. |
| 5,520,666 A | 5/1996 | Choudhury et al. |
| 5,542,932 A | 8/1996 | Daugherty |
| 5,549,566 A | 8/1996 | Elias et al. |
| 5,549,576 A | 8/1996 | Patterson et al. |
| 5,549,577 A | 8/1996 | Siegel et al. |
| 5,562,631 A | 10/1996 | Bogert |
| 5,562,633 A | 10/1996 | Wozencroft |
| 5,573,510 A | 11/1996 | Isaacson |
| 5,575,769 A | 11/1996 | Vaillancourt |
| 5,575,777 A | 11/1996 | Cover et al. |
| 5,584,809 A | 12/1996 | Gaba |
| 5,599,310 A | 2/1997 | Bogert |
| 5,601,536 A | 2/1997 | Crawford et al. |
| 5,613,663 A | 3/1997 | Schmidt et al. |
| 5,651,772 A | 7/1997 | Arnett |
| 5,657,963 A | 8/1997 | Hinchliffe et al. |
| 5,676,656 A | 10/1997 | Brimhall |
| 5,690,612 A | 11/1997 | Lopez et al. |
| 5,690,619 A | 11/1997 | Erskine |
| 5,697,907 A | 12/1997 | Gaba |
| 5,697,914 A | 12/1997 | Brimhall |
| 5,697,915 A | 12/1997 | Lynn |
| 5,699,821 A | 12/1997 | Paradis |
| 5,700,244 A | 12/1997 | Kriesel |
| 5,700,250 A | 12/1997 | Erskine |
| 5,704,919 A | 1/1998 | Kraus et al. |
| 5,718,688 A | 2/1998 | Wozencroft |
| 5,730,123 A | 3/1998 | Lorenzen et al. |
| 5,738,144 A | 4/1998 | Rogers |
| 5,749,856 A | 5/1998 | Zadini et al. |
| 5,749,861 A | 5/1998 | Guala et al. |
| 5,772,636 A | 6/1998 | Brimhall et al. |
| 5,800,399 A | 9/1998 | Bogert et al. |
| 5,806,831 A | 9/1998 | Paradis |
| 5,810,780 A * | 9/1998 | Brimhall ........... A61M 25/0693 604/167.02 |
| 5,817,069 A | 10/1998 | Arnett |
| 5,843,046 A | 12/1998 | Motisi et al. |

(56) References Cited

U.S. PATENT DOCUMENTS

| | | | |
|---|---|---|---|
| 5,853,393 A | 12/1998 | Bogert | |
| 5,882,345 A | 3/1999 | Yoon | |
| 5,911,710 A | 6/1999 | Barry et al. | |
| 5,935,109 A | 8/1999 | Donnan | |
| 5,935,110 A | 8/1999 | Brimhall | |
| 5,947,932 A | 9/1999 | Desecki et al. | |
| 5,954,698 A | 9/1999 | Pike | |
| 5,961,497 A | 10/1999 | Larkin | |
| 5,967,490 A | 10/1999 | Pike | |
| 6,039,302 A | 3/2000 | Cote, Sr. et al. | |
| 6,056,726 A | 5/2000 | Isaacson | |
| 6,077,244 A | 6/2000 | Botich et al. | |
| 6,117,108 A | 9/2000 | Woehr et al. | |
| 6,142,981 A | 11/2000 | Heck et al. | |
| 6,156,010 A | 12/2000 | Kuracina et al. | |
| 6,171,287 B1 | 1/2001 | Lynn et al. | |
| 6,206,851 B1 | 3/2001 | Prosl | |
| 6,221,047 B1 | 4/2001 | Greene et al. | |
| 6,224,569 B1 | 5/2001 | Brimhall | |
| 6,273,869 B1 | 8/2001 | Vaillancourt | |
| 6,287,278 B1 | 9/2001 | Woehr et al. | |
| D451,599 S | 12/2001 | Crawford et al. | |
| D451,600 S | 12/2001 | Crawford et al. | |
| 6,379,332 B1 | 4/2002 | Van Landuyt | |
| D458,678 S | 6/2002 | Cindrich | |
| D458,994 S | 6/2002 | Cindrich | |
| 6,440,119 B1* | 8/2002 | Nakada | A61M 25/0014 604/500 |
| 6,461,362 B1 | 10/2002 | Halseth et al. | |
| 6,485,473 B1 | 11/2002 | Lynn | |
| 6,497,994 B1 | 12/2002 | Kafrawy | |
| 6,506,181 B2 | 1/2003 | Meng et al. | |
| D469,870 S | 2/2003 | Niermann et al. | |
| 6,565,542 B2 | 5/2003 | Kumar | |
| 6,575,960 B2 | 6/2003 | Becker et al. | |
| 6,595,954 B1 | 7/2003 | Luther et al. | |
| 6,595,981 B2 | 7/2003 | Huet | |
| 6,616,630 B1 | 9/2003 | Woehr | |
| 6,652,486 B2 | 11/2003 | Bialecki et al. | |
| 6,663,592 B2 | 12/2003 | Rhad et al. | |
| 6,689,102 B2 | 2/2004 | Greene | |
| 6,695,814 B2 | 2/2004 | Greene et al. | |
| 6,699,221 B2 | 3/2004 | Vaillancourt | |
| 6,709,419 B2 | 3/2004 | Woehr | |
| 6,719,726 B2 | 4/2004 | Meng et al. | |
| 6,740,063 B2 | 5/2004 | Lynn | |
| D491,266 S | 6/2004 | Cindrich et al. | |
| D492,031 S | 6/2004 | Cindrich et al. | |
| 6,749,588 B1 | 6/2004 | Howell et al. | |
| D492,774 S | 7/2004 | Cindrich et al. | |
| 6,837,884 B2 | 1/2005 | Woloszko | |
| 6,883,778 B1 | 4/2005 | Newton et al. | |
| 7,008,404 B2 | 3/2006 | Nakajima | |
| 7,347,839 B2 | 3/2008 | Hiejima | |
| 7,396,346 B2 | 7/2008 | Nakajima | |
| 7,470,254 B2 | 12/2008 | Basta et al. | |
| D592,302 S | 5/2009 | Stokes et al. | |
| 7,670,317 B2 | 3/2010 | Cindrich et al. | |
| 7,694,403 B2 | 4/2010 | Moulton | |
| 7,736,339 B2 | 6/2010 | Woehr et al. | |
| 7,905,856 B2 | 3/2011 | McGuckin, Jr. et al. | |
| 7,914,494 B2 | 3/2011 | Hiejima | |
| 8,066,670 B2 | 11/2011 | Cluff et al. | |
| 8,066,675 B2 | 11/2011 | Cindrich et al. | |
| 8,070,725 B2 | 12/2011 | Christensen | |
| 8,357,119 B2 | 1/2013 | Stout et al. | |
| 8,361,020 B2 | 1/2013 | Stout et al. | |
| 8,388,583 B2 | 3/2013 | Stout et al. | |
| 8,574,203 B2 | 11/2013 | Stout et al. | |
| 8,597,252 B2 | 12/2013 | Burkholz et al. | |
| 8,641,675 B2 | 2/2014 | Stout et al. | |
| 8,679,063 B2 | 3/2014 | Stout et al. | |
| D713,522 S | 9/2014 | Woehr et al. | |
| D819,802 S | 6/2018 | Burkholz et al. | |
| D835,262 S | 12/2018 | Burkholz et al. | |
| D837,368 S | 1/2019 | Burkholz et al. | |
| 2001/0053895 A1 | 12/2001 | Vaillancourt | |
| 2002/0072712 A1 | 6/2002 | Nool et al. | |
| 2002/0082546 A1 | 6/2002 | Crank et al. | |
| 2002/0177814 A1 | 11/2002 | Meng et al. | |
| 2003/0083620 A1 | 5/2003 | Luther et al. | |
| 2004/0078003 A1 | 4/2004 | Smith et al. | |
| 2004/0092889 A1 | 5/2004 | Ferguson et al. | |
| 2004/0102735 A1 | 5/2004 | Moulton et al. | |
| 2004/0181192 A1 | 9/2004 | Cuppy | |
| 2004/0193112 A1 | 9/2004 | Glazier et al. | |
| 2004/0204681 A1 | 10/2004 | Thoresen et al. | |
| 2004/0225260 A1 | 11/2004 | Villa et al. | |
| 2004/0243060 A1 | 12/2004 | Rossi et al. | |
| 2004/0243061 A1 | 12/2004 | McGurk | |
| 2005/0273019 A1 | 12/2005 | Conway et al. | |
| 2005/0277879 A1 | 12/2005 | Daga | |
| 2006/0163515 A1 | 7/2006 | Ruschke | |
| 2007/0043334 A1 | 2/2007 | Guala | |
| 2007/0083157 A1 | 4/2007 | Belley et al. | |
| 2007/0083162 A1 | 4/2007 | O'Reagan et al. | |
| 2007/0093778 A1 | 4/2007 | Cindrich et al. | |
| 2007/0191777 A1 | 8/2007 | King | |
| 2007/0225648 A1 | 9/2007 | Winsor et al. | |
| 2007/0233007 A1 | 10/2007 | Adams | |
| 2008/0039796 A1 | 2/2008 | Nakajima | |
| 2008/0108944 A1 | 5/2008 | Woehr et al. | |
| 2008/0132832 A1 | 6/2008 | McKinnon et al. | |
| 2008/0167577 A1 | 7/2008 | Weilbacher et al. | |
| 2008/0255473 A1 | 10/2008 | Dalebout et al. | |
| 2008/0287906 A1 | 11/2008 | Burkholz et al. | |
| 2009/0054845 A1 | 2/2009 | Puhasmagi et al. | |
| 2009/0099431 A1 | 4/2009 | Dalebout et al. | |
| 2009/0287189 A1 | 11/2009 | Suwito | |
| 2010/0204648 A1 | 8/2010 | Stout et al. | |
| 2010/0204675 A1 | 8/2010 | Woehr et al. | |
| 2010/0222746 A1 | 9/2010 | Burkholz | |
| 2010/0280455 A1* | 11/2010 | Ogawa | A61M 5/158 604/164.01 |
| 2011/0046570 A1 | 2/2011 | Stout et al. | |
| 2011/0054403 A1 | 3/2011 | Tanabe et al. | |
| 2011/0130728 A1 | 6/2011 | McKinnon | |
| 2012/0016265 A1 | 1/2012 | Peterson et al. | |
| 2012/0016307 A1 | 1/2012 | Burkholz et al. | |
| 2012/0053523 A1 | 3/2012 | Harding | |
| 2013/0090608 A1 | 4/2013 | Stout et al. | |
| 2013/0218082 A1 | 8/2013 | Hyer et al. | |
| 2013/0237925 A1 | 9/2013 | Trainer et al. | |
| 2014/0046258 A1 | 2/2014 | Stout et al. | |
| 2014/0107584 A1 | 4/2014 | Rosenberg et al. | |
| 2014/0364809 A1 | 12/2014 | Isaacson et al. | |
| 2015/0224296 A1 | 8/2015 | Winsor | |
| 2017/0120008 A1 | 5/2017 | Burkholz et al. | |
| 2017/0120014 A1 | 5/2017 | Harding et al. | |
| 2017/0216535 A1 | 8/2017 | Mao | |
| 2017/0347913 A1 | 12/2017 | Isaacson et al. | |

FOREIGN PATENT DOCUMENTS

| | | |
|---|---|---|
| CN | 102440822 A | 5/2012 |
| CN | 102716541 A | 10/2012 |
| CN | 203852671 | 10/2014 |
| DE | 20 2009 009 602 U1 | 12/2009 |
| EP | 0 268 480 A1 | 5/1988 |
| EP | 0 732 120 A1 | 9/1996 |
| EP | 0 812 601 A2 | 12/1997 |
| EP | 0 993 839 A1 | 4/2000 |
| EP | 1 306 097 | 5/2003 |
| EP | 1 679 043 A1 | 7/2006 |
| EP | 1 884 257 A1 | 2/2008 |
| EP | 1 944 049 A1 | 7/2008 |
| EP | 2022421 | 2/2009 |
| EP | 2 044 970 A1 | 4/2009 |
| EP | 2 327 434 A1 | 6/2011 |
| GB | 2508466 A | 6/2014 |
| JP | S56102253 | 8/1981 |
| JP | S5832774 | 2/1983 |
| JP | H06-086821 | 3/1994 |
| JP | H09-509075 | 9/1997 |

(56) References Cited

FOREIGN PATENT DOCUMENTS

| | | |
|---|---|---|
| JP | 2000279527 | 10/2000 |
| JP | 2004528127 | 9/2004 |
| JP | 2011045544 | 3/2011 |
| JP | 2012521796 | 9/2012 |
| JP | 2012200425 | 10/2012 |
| JP | 3188771 | 1/2014 |
| JP | 2014108112 | 6/2014 |
| WO | 88/07388 A1 | 10/1988 |
| WO | 97/45151 | 12/1997 |
| WO | 98/42393 A1 | 10/1998 |
| WO | 99/34849 A1 | 7/1999 |
| WO | 01/12254 A1 | 2/2001 |
| WO | 02/096495 | 12/2002 |
| WO | 2004/032995 A2 | 4/2004 |
| WO | 2004/082727 | 9/2004 |
| WO | 2004/087247 | 10/2004 |
| WO | 2004/098685 A1 | 11/2004 |
| WO | 2006/037638 A1 | 4/2006 |
| WO | 2007/052655 | 5/2007 |
| WO | 2008/022258 A2 | 2/2008 |
| WO | 2008/045761 A2 | 4/2008 |
| WO | 2008/052790 A2 | 5/2008 |
| WO | 2008/058132 A2 | 5/2008 |
| WO | 2008/058133 A2 | 5/2008 |
| WO | 2009/114833 A1 | 9/2009 |
| WO | 2010/093791 A1 | 8/2010 |
| WO | 2010/111283 | 9/2010 |
| WO | 2010/111285 A1 | 9/2010 |
| WO | 2011/055287 | 5/2011 |
| WO | 2011/109542 A1 | 9/2011 |
| WO | 2016/007442 | 1/2016 |
| WO | 2017/062579 | 4/2017 |

* cited by examiner

INTEGRATED CATHETER WITH INDEPENDENT FLUID PATHS

RELATED APPLICATIONS

This application claims the benefit of U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application No. 62/247,617, which was filed on Oct. 28, 2015, U.S. Provisional Patent Application Ser. No. 62/247,607, which was filed Oct. 28, 2015, U.S. Provisional Patent Application Ser. No. 62/247,621, which was filed Oct. 28, 2015, U.S. Provisional Patent Application Ser. No. 62/247,624, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

BACKGROUND OF THE INVENTION

This disclosure relates generally to intravenous catheters (e.g., vascular access devices). More specifically, this application discloses various methods for using and systems of integrated catheter assemblies with independent fluid paths. In general, vascular access devices are inserted into veins via peripheral or central vessels for diagnostic or therapeutic reasons. Vascular access devices can be used for infusing fluid (e.g., saline solution, blood, medicaments, and/or total parenteral nutrition) into a patient, withdrawing fluids (e.g., blood) from a patient, and/or monitoring various parameters of the patient's vascular system. Additionally, a convention is followed in this disclosure using the term "proximal" to refer to a portion of a device closest to the medical practitioner and the term "distal" for the portion of the device toward a patient or away from the medical practitioner.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a venipuncture needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the sharp distal tip of the introducer needle extends beyond the distal tip of the catheter. Moreover, the catheter and needle are often assembled so that during insertion, the bevel of the needle faces up, away from the patient's skin. The catheter and introducer needle are generally inserted at a shallow angle through the patient's skin into a blood vessel.

Following insertion of the catheter and introducer needle into the blood vessel at the catheterization site, the introducer needle is removed leaving the catheter in the blood vessel. The catheter can then be used to infuse fluids into the vasculature of the patient. The removed introducer needle is considered a "blood-contaminated sharp" and must then be properly handled and discarded.

Although conventional over-the-needle catheters may provide a variety of benefits, they are not without their shortcomings. For example, after the introducer needle is removed, it can present a needle stick hazard to the medical practitioner and/or patient. Also, in placing the catheter, the medical practitioner must take care to ensure that the introducer needle (and the catheter) has been inserted sufficiently to enter the blood vessel without puncturing through the vein.

Thus, while a variety of over-the-needle catheters currently exist, challenges still exist, including those listed above. Accordingly it would be an improvement in the art to augment or even replace current systems and techniques with other systems and techniques.

BRIEF SUMMARY OF THE INVENTION

This disclosure generally relates to catheter systems with independent fluid paths. More specifically, this disclosure discusses catheter systems that provide primary and secondary blood flashback to indicate that a needle of the catheter system has entered a blood vessel of a patient. Methods of using these catheter systems are also discussed.

Some exemplary catheter systems comprise a catheter adapter comprising a catheter hub comprising a distal end and a proximal end and defining a chamber extending between the distal end and the proximal end, a catheter extending from the distal end of the catheter hub and in fluid communication with the chamber, a stabilization platform, and a needle hub comprising a needle configured to slidably fit within the catheter, a needle hub body anchored to a proximal end of the needle, where in an insertion configuration, the proximal end of the catheter hub is removably coupled within a distal opening of the needle hub, and where after placement of the catheter, the needle huh is retracted from the catheter adapter to slidably remove the needle from the catheter and to separate the needle hub from the catheter adapter. In some embodiments, the needle comprises an axial channel configured provide a primary blood flashback in the chamber of the catheter hub to indicate that the needle has entered a vasculature of a patient. In other embodiments, the needle comprises an open bore in fluid communication with a chamber of the needle hub and wherein blood flows through the open bore to the chamber of the needle hub to provide a secondary blood flashback that indicates that the needle has entered a vasculature of a patient.

In some cases, the stabilization platform can further comprise a first wing comprising a generally planar shape to stably maintain the catheter adapter against a skin of a patient. In other cases, the stabilization platform can further comprise a soft push tab configured to provide a grasping surface to manipulate and advance the catheter adapter. In yet other cases, the catheter hub can further comprise a Y-port in fluid communication with the chamber of the catheter hub. In some instances, the needle hub can further comprise a paddle grip extending from a distal end of the needle huh and configured to provide a grip surface to manipulate the needle huh. In other instances, catheter hub can further comprise a septum configured such that the needle can removably and slidably pass through a slit in the septum. In yet other instances, the catheter hub can further comprise a septum canister configured to secure the septum in the catheter hub. In another instance, the catheter system can further comprise a needle safety configured protect against needle sticks by engaging a distal point of the needle as the needle is retracted from the catheter adapter.

In some embodiments, the methods can include methods of catheterization comprising providing a catheter system comprising a catheter adapter comprising a catheter hub defining a chamber extending between a distal end and a proximal end, a catheter extending from the distal end of the catheter hub and in fluid communication with the chamber, and a stabilization platform, and a needle hub comprising a needle configured to slidably fit within the catheter and a needle hub body anchored to a proximal end of the needle, inserting the needle and catheter at a catheter insertion site, advancing the needle and catheter at the catheter insertion site until a primary blood flashback is provided in the chamber of the catheter hub via an axial channel on the needle, securing the catheter at the catheter insertion site, and retracting the needle hub from the catheter adapter to slidably remove the needle from the catheter and to separate the needle hub from the catheter adapter. In other embodiments, the method further comprises advancing the needle and catheter at the catheter insertion site until a secondary blood flashback is provided in a chamber of the needle hub. In yet other embodiments, securing the catheter further comprises securing the stabilization platform against skin proximate to the catheter insertion site. In some embodiments, the method further comprises engaging a needle safety on a distal point of the needle as the needle is retracted from the catheter adapter.

In some embodiments, the catheter system comprises a catheter adapter comprising a catheter hub defining a chamber extending between a distal end and a proximal end of the catheter huh and a catheter extending from the distal end of the catheter hub and in fluid communication with the chamber and a stabilization platform comprising a first wing and a soft push tab, and a needle hub comprising a needle configured to slidably fit within the catheter and a needle hub body anchored to a proximal end of the needle, where in an insertion configuration, a proximal extension of the catheter hub is removably coupled within a distal opening of the needle hub, and where after placement of the catheter, the needle hub is retracted from the catheter adapter to slidably remove the needle from the catheter and to separate the needle hub from the catheter adapter. In other embodiments, the needle comprises an axial channel configured provide a primary blood flashback to indicate that the needle has entered a blood vein. In yet other embodiments, blood flows through an open bore of the needle to the chamber of the needle huh to provide a secondary blood flashback to indicate that the needle has entered a vasculature of a patient.

In some cases, the catheter hub can further comprise a septum with a slit, wherein the slit is configured to allow the needle to slidably pass therethrough, and wherein the slit is configured to conform to the axial channel while the axial chum slidably passes through the slit to exclude any fluid in the axial channel. In other cases, the catheter hub can further comprise a septum canister configured to secure the septum in the catheter hub and wherein the septum canister comprises a retaining ridge configured to secure the septum canister to the catheter hub. In yet other cases, the system can further comprise a needle safety removably disposed within the proximal extension of the catheter hub and configured protect against needle sticks by engaging a distal point of the needle as the needle is retracted from the catheter adapter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the prose invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

In general, this disclosure relates to catheter systems and methods of catheterization using such catheter systems. In some instances, a catheter system can comprise a catheter adapter and a needle hub arranged along a longitudinal axis. The catheter hub can comprise an over-the-needle catheter configured for catheterization of a patient. The needle hub can comprise a needle anchored to a needle hub body. The needle can be slidably fitted within the catheter in an insertion configuration. The needle hub can be separated from the catheter adapter to slidably remove the needle from the catheter. Using gripping surfaces on the catheter adapter and the needle hub, a medical practitioner can insert the over-the-needle catheter into a vasculature of the patient at a catheter insertion site. When the needle enters a blood vessel, an axial channel on the needle provides a primary blood flash to inform the medical practitioner that the needle has entered the blood vessel. The medical practitioner can then secure the catheter in place and can retract and separate the needle hub from the catheter adapter to slidably remove the needle from the catheter. Blood flowing through an open bore of the needle to a chamber of the needle hub can provide a secondary blood flash to also inform the medical practitioner that the needle has entered the blood vessel. As the needle is slidably removed from the catheter, a needle safety can engage on a distal point of the needle to prevent an inadvertent needle stick.

Figure 1:
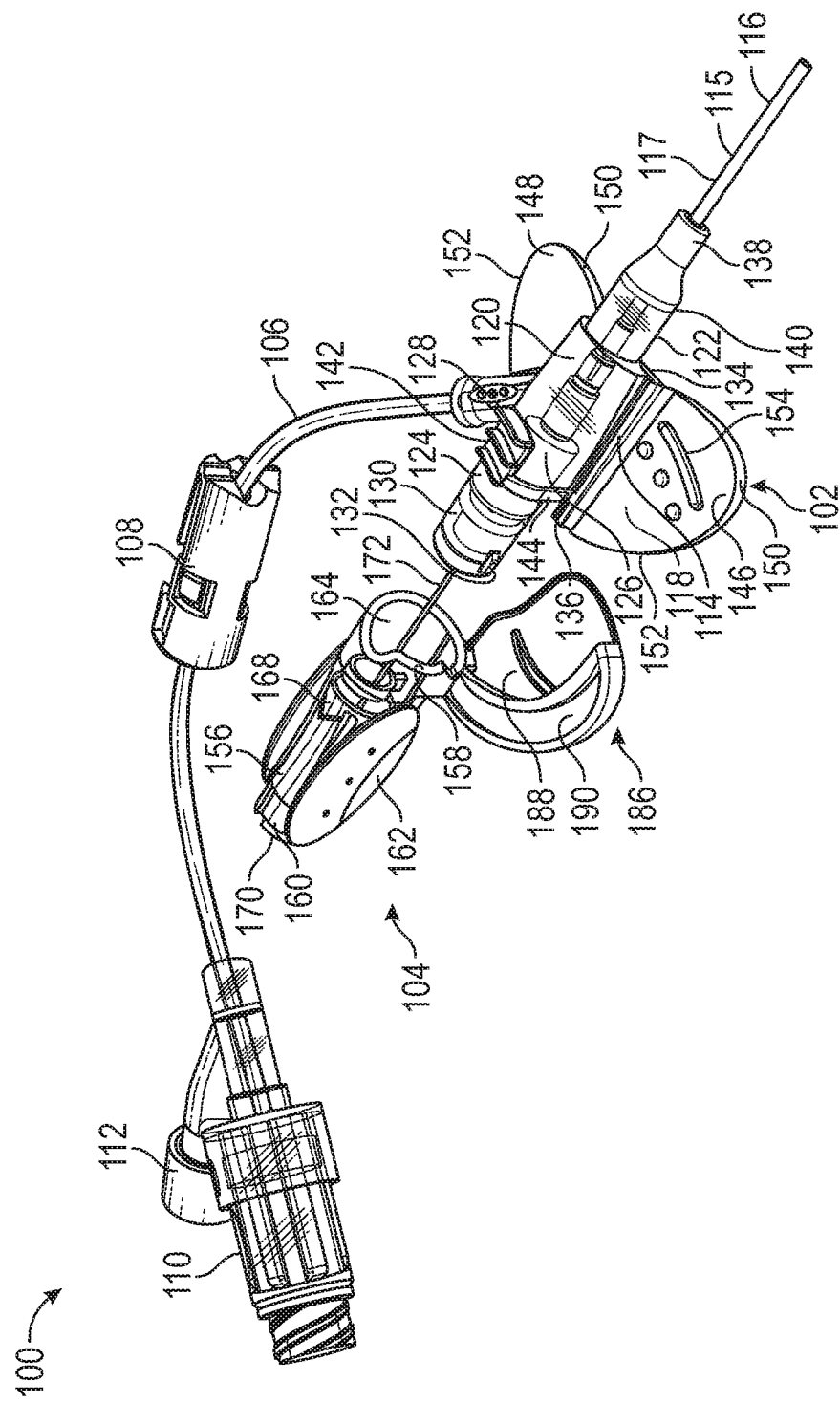
FIG. 1 is a perspective view of a catheter system, according to some embodiments.

Referring now to FIG. 1, a catheter system 100 is shown. The catheter system 100 can be configured to be connected to an intravenous fluid and/or a medicament and to infuse that intravenous fluid and/or medicament into a vasculature of a patient. While the catheter system 100 can comprise any suitable component and/or suitable structure, at least in some embodiments, it comprises a catheter adapter 102, a needle hub 104, and an extension tubing 106. The catheter adapter 102 can be inserted in the vasculature of the patient at a catheter insertion site with the aid of the needle hub 104. In some cases, the extension tubing 106 can be fluidically coupled with the catheter adapter 102 and can be configured to convey the intravenous fluid from a supply of the intravenous fluid into the vasculature of the patient via the inserted catheter adapter 102. In other cases, the extension tubing can comprise a clamp 108 configured to manually block or permit flow of the intravenous fluid to the catheter adapter 102. The extension tubing 106 can also comprise a luer fitting 110 configured to readily connect the extension tubing 106 with the supply of the intravenous fluid (e.g., an IV solution bag). In yet other cases, the extension tubing 106 can comprise a sampling port 112 configured to provide a medical practitioner with access to the vasculature of the patient through extension tubing 106. For example, the medical practitioner can draw a blood sample from the patient using the sampling port 112 and/or can infuse a medicament into the vasculature of the patient directly through the sampling port 112. FIG. 1 shows the catheter system 100 with the needle hub 104 partially retracted from the catheter adapter 102.

In some embodiments, the catheter adapter 102 comprises a catheter hub 114 fluidically coupled to a catheter 115. The catheter 115 can comprise a distal end 116 configured to enter the patient's vasculature. The catheter 115 can also comprise a proximal end 117 fluidically connected with the catheter hub 114. The catheter adapter 102 can also comprise a stabilization platform 118 and a catheter hub body 120. In some cases, the catheter hub 120 comprises a generally tubular and/or hollow configuration and can have a distal end 122 and a proximal end 124. in other cases, the catheter hub body 120 can define a chamber 126 that runs the length of the catheter hub 120. The catheter hub 120 can also comprise a Y-port 128 that fluidically couples the catheter hub 120 with the extension tubing 106. In yet other cases, the catheter hub body 120 can comprise a proximal extension 130 with a proximal extension tab 132. The proximal extension 130 can be configured to slidably couple with the needle hub 104. The proximal extension 132 can prevent and/or limit the rotational movement of the needle hub 104 with respect to the catheter adapter 102 when the proximal extension 130 is slidably coupled with the needle hub 104.

In some embodiments, the stabilization platform 118 comprises a generally planar configuration adapted to resting flat against a skin of the patient proximal to the catheter insertion site. The stabilization platform 118 can permit the stabilization platform 118 and/or the catheter hub 114 to be secured against the patient's skin to allow the catheter adapter 102 to be stably maintained in position during infusion. The stabilization platform 118 can comprise a distal end 134 and a proximal end 136 and can be disposed at least partially below the catheter hub body 120. The stabilization platform 118 can comprise a strain relief coupling 138 configured to couple the proximal end 117 of the catheter 115 to the chamber 126 of the catheter hub body 120. In some cases, the strain relief coupling 138 can be configured as a soft compliant material that permits the catheter 115 to bend with respect to the catheter hub body 120. In other cases, the strain relief coupling 138 can be configured as a stiff compliant material that limits the catheter 115 from bending with respect to the catheter hub body 120. In yet other cases, the stabilization platform 118 can comprise a strain relief connecting tab 140 configured to couple at least a portion of the strain relief coupling 138 to the distal end 134 of the stabilization platform 118.

In some embodiments, the stabilization platform 118 comprises a soft push tab 142 configured to provide a grasping surface for the medical practitioner to grasp while manipulating and advancing the catheter system 100. In some cases, the medical practitioner can place his or her thumb on the soft push tab 142 as he or she grasps the catheter hub 114 and inserts the catheter 115. In other cases, the stabilization platform 118 can be disposed on top of the catheter hub body 120 and can comprise soft push tab connectors 144 configured to couple the soft push tab 142 to the proximal end 136 of the stabilization platform 118.

In some embodiments, the stabilization platform 118 comprises a first wing 146 with a generally planar shape. The stabilization platform 118 can also comprise a second wing 148 that also has a generally planar shape that can be generally coplanar with the first wing 146. The second wing 148 can be disposed on an opposite side of the catheter hub 114 from the first wing 146. In some cases, the first wing 146 and the second wing 148 can extend from opposite sides of the catheter hub 114. While the first wing 146 and the second wing 148 can comprise any suitable shape, at lease in some cases, when viewed from above the catheter hub 114, the first wing 146 and the second wing 148 each comprise a generally triangular shape. In other cases, the first wing 146 and the second wing 148 can comprise triangular, rounded triangular, rectangular, and rounded rectangular shapes. In yet other cases, the first wing 146 and the second wing 148 can comprise circular, semi-circular, oval, oblong, and other suitable shapes. The first wing 146 and the second wing 148 can comprise leading edges 150 oriented towards the distal end 134 of the stabilization platform 118. The first wing 146 and the second wing 148 can comprise trailing edges 152 oriented towards the proximal end 136 of the stabilization platform 118. One or more of the first wing 146 and the second wing 148 can comprise gripping features 154. The grip features 154 can be configured to provide grasping surfaces for the medical practitioner to manipulate the catheter system 100. In other embodiments, the stabilization platform 118 comprises a hardness suitable to allow the stabilization platform 118 to function as intended. For example, in some cases, the stabilization platform 118 comprises a material durometer range of about 30 Shore A to about 90 Shore D. In other cases, the stabilization platform 118 comprises a material durometer range of about 50 Shore A to about 90 Shore A.

In some embodiments, the needle hub 104 comprises a needle hub body 156. The needle hub body 156 can comprise a generally tubular shape with a distal end 158 and a proximal end 160. The needle hub body 156 can also comprise grip surfaces 162 configured to provide grasping surfaces for the medical practitioner to manipulate the catheter system 100 and/or to retract the needle hub 104 from the catheter adapter 102. In some instances, the needle hub body 156 can comprise a distal opening 164 configured to slidably receive the proximal extension 130 of the catheter hub body 120. In yet other instances, the needle hub body 156 defines a chamber 168 that extends from the distal opening 164 to a proximal opening 170. The needle hub 104 can also comprise a paddle grip 186 that extends from the distal end 158 of the needle hub 104. The paddle grip 186 can comprise a generally planar shape and can be generally coplanar with the first 146 and/or the second wing 148. The paddle grip 186 can also comprise a grip surface 188 configured to provide gripping surfaces for the medical practitioner to manipulate the catheter system 100 and/or the needle hub 104 and/or to retract the needle hub 104 from the catheter adapter 102. The paddle grip 186 can comprise a lip 190 configured to receive a trailing edge 152 of the first wing 146 and/or the second wing 148. In some instances, a bottom portion of the first wing 146 and/or the second wing 148 can be received by a top portion of the paddle grip 186.

In some embodiments, the needle hub 104 comprises a needle 172. The needle 172 can be mounted in the needle hub body 156 and can extend through the distal opening 164. The needle 172 can be configured to removably and slidably pass through a septum 200 (not shown) in the chamber 126 of the catheter hub body 120, traverse the chamber 126, and removably and slidably pass through the catheter 115.

Figure 2A:
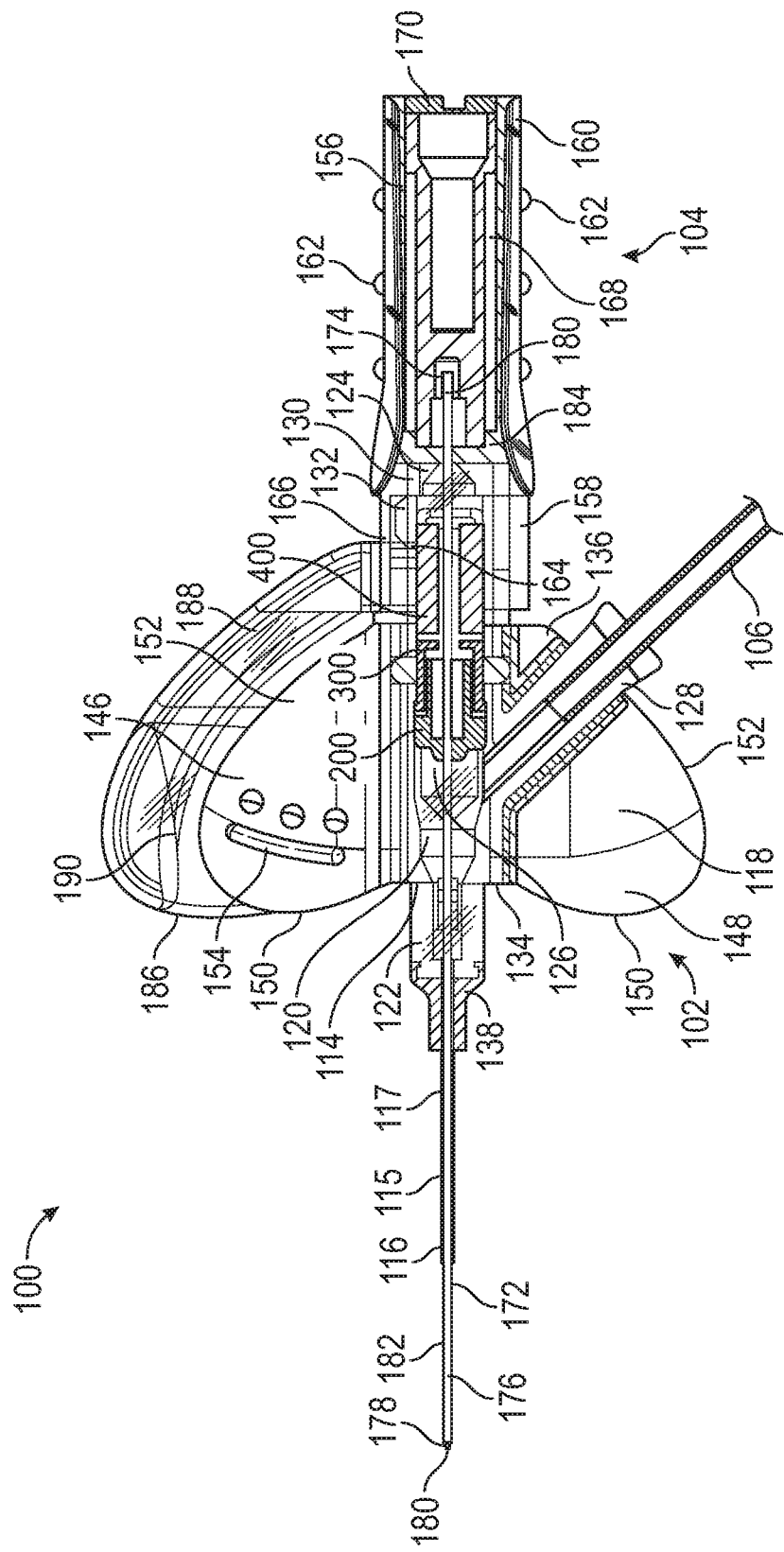
FIG. 2A is a top cutaway view of a catheter system, according to some embodiments.
Figure 2B:
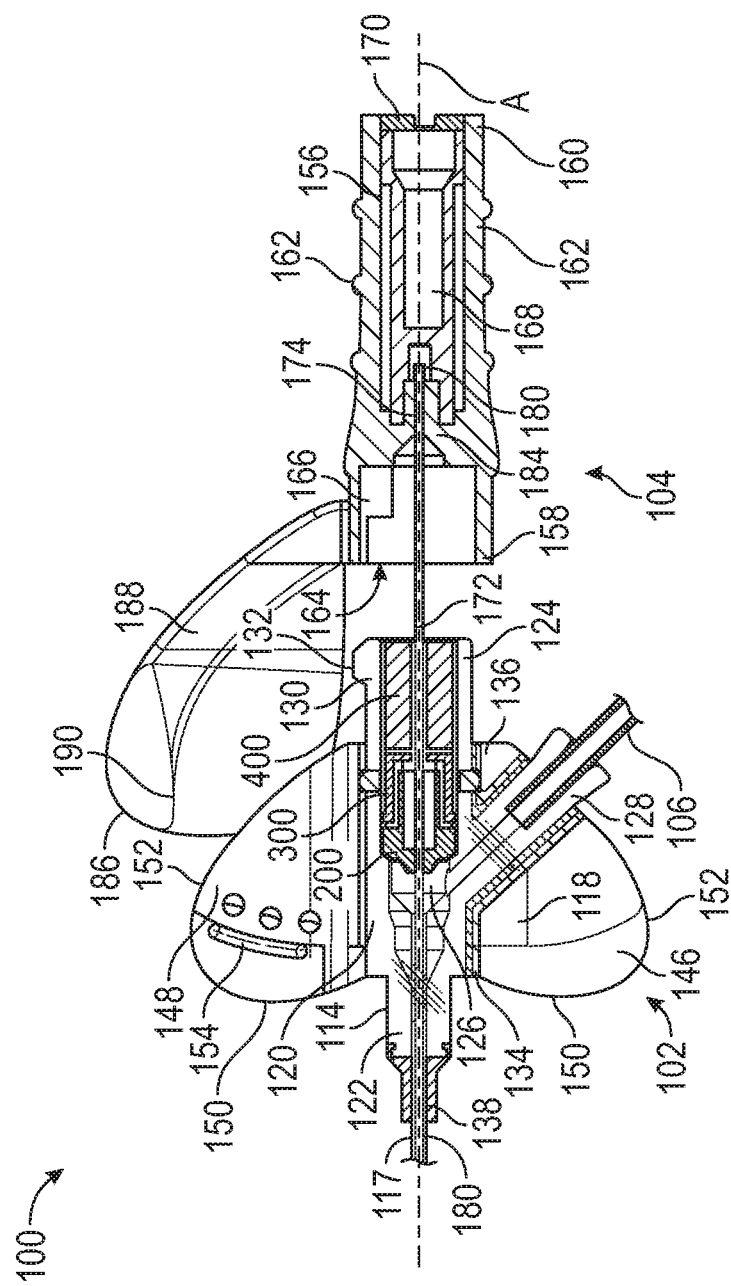
FIG. 2B is a top cutaway view of a catheter system, according to some embodiments.

Referring now to FIGS. 2A and 2B, cutaway views of the catheter system 100 is illustrated. FIG. 2A illustrates the catheter system 100 in an insertion configuration, in which the catheter system 100 is ready to be used to position the catheter 115 into the vasculature of the patient. When in the insertion configuration as shown in FIG. 2A, the proximal extension 130 of the catheter hub body 120 is slidably received within the distal opening 164 of the needle hub body 156. As seen in FIG. 2A, the distal opening 164 can also comprise a distal opening groove 166 configured to slidably receive the proximal extension tab 132 of the proximal extension 130. The distal opening groove 166 can be configured such when the proximal extension tab 132 is engaged with the distal opening groove 166, the rotational movement of the catheter adapter 102 with respect to the needle hub 104 is prevented or limited. In other instances, when the proximal extension tab 132 is engaged with the distal opening groove 166, the rotational movement of the catheter adapter 102 with respect to the needle hub 104 is limited to a specific range of rotational motion.

As shown in FIG. 2A, when the catheter system 100 is in the insertion configuration, the paddle grip 186 slidably receives the first wing 146. In the insertion configuration, the trailing edge 152 of the first wing 146 can be disposed proximally to the lip 190 of the paddle grip 186 and the grip surface 188 of the paddle grip 186. In some cases, the trailing edge 152 of the first wing 146 can abut the lip 190 of the paddle grip 186.

With continued reference to FIG. 2A, in the insertion configuration, the needle 172 removably and slidably passes through the catheter 115 and extends through the catheter 115 past the distal end 116 of the catheter 115. The needle 172 can comprise a proximal end 174 and a distal point 176. The distal point 176 can comprise a beveled opening 178 configured to pierce the skin of the patient at the catheter insertion site. The needle 172 can comprise an open bore 180 therethrough. The needle 172 can also comprise an axial channel 182 beginning at the distal point 176 and continuing along at least a portion of a length of the needle 172. The needle 172 can removably and slidably pass through the septum 200, a septum canister 300, and a needle safety 400, The septum canister is configured to be disposed within the chamber 126 of the catheter hub body 120. Likewise, the septum canister 300 is configured to be disposed within the chamber 126 of the catheter hub body 120 and to secure the septum 200 in place. The needle safety 400 can be disposed at least in part in the proximal extension 130 of the catheter hub body 120. The needle 172 can further extend into the distal opening 164 of the needle hub body 156. The needle 172 can be anchored to the needle hub 104 by a needle mount 184 within the needle hub body 156. The proximal end 174 of the needle 172 can be disposed within the chamber 168 with the open bore 180 opening into the chamber 168. Thus, the open bore 180 of the needle 172 allows fluid entering the beveled opening 178 to be in fluidic communication with the chamber 168 and the proximal chamber opening 170.

In some embodiments, the medical practitioner inserts the catheter system 100 into the patient's vasculature whet the catheter system 100 is in the insertion configuration. The medical practitioner can grasp the catheter system 100 by one or more gripping surfaces (e.g., the soft push tab 142, the grip features 154, the grip surfaces 162, and the grip surface 188) and manipulate the catheter system 100 into a position proximate the catheter insertion site. The medical practitioner can then pierce the skin of the patient with the beveled opening 178 of the needle 172 and can advance the needle 172 through tissue of the patient until the vasculature (e.g., a vein) of the patient is reached by the needle 172 and the catheter 115. Once the vasculature of the patient is reached, the medical practitioner can retract the needle 172 by removing the needle 172 from the catheter 115 while leaving the catheter 115 inserted into the vasculature. While retracting the needle 172, the medical practitioner can maintain the catheter 115 in position by holding the catheter adapter 102 in position via one or more of the soft push tab 142 and the grip features 154. The medical practitioner can retract the needle by grasping the grip surfaces 162 of the needle hub body 156 and slidably removing the needle 172 in a proximal direction towards the medical practitioner. In some cases, after the needle 172 has advanced into the vasculature of the patient, the medical practitioner can advance the distal end 116 of the catheter 115 into the vasculature of the patient by maintaining the needle 172 in position and slidably advancing the distal end 116 into the vasculature of the patient. Once the catheter 115 is inserted into the vasculature of the patient, the needle 172 can be retracted as described above.

Referring now to FIG. 2B, a cutaway view of the catheter system 100 is shown with the needle hub 104 partially retracted from the catheter adapter 102. The needle hub 104 can be translated longitudinally along an axis "A" to separate the needle bob 104 from the catheter adapter 102 and to slidably remove the needle 172 from the catheter 115. As the needle hub 104 is retracted, the proximal extension 130 of the catheter hub body 120 slidably disengages from the distal opening 164 of the needle hub body 156. Likewise, the first wing 146 separates from the paddle grip 186. As the needle hub 104 is retracted from the catheter adapter 102, the needle 172 is slidably removed from the catheter 115, the septum 200, and the septum canister 300. As described in more detail below, the distal point 176 of the needle 172 slidably passes into the needle safety 400 and is engaged by the needle safety 400. The engaged needle safety 400 is retained on the distal point 176 of the needle 172 and the needle safety 400 is removably disengaged from the catheter adapter 102 (See FIG. 6) thereby protecting the medical practitioner from an inadvertent needle stick.

Figure 3A:
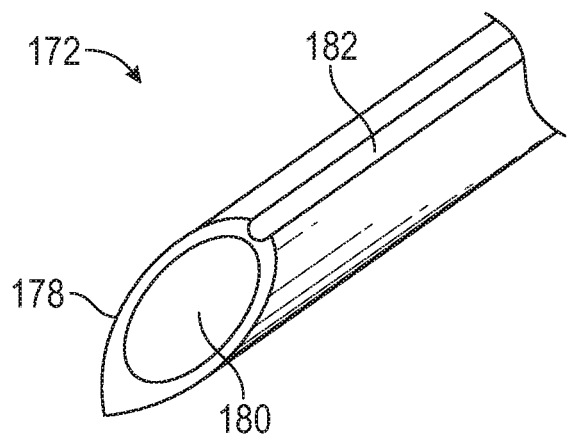
FIG. 3A is a perspective view of a needle, according to some embodiments.
Figure 3B:
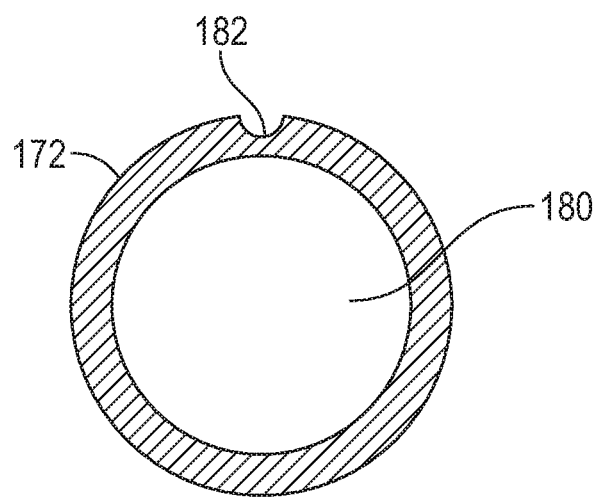
FIG. 3B is a cross-sectional view of the needle of FIG. 3A, according to some embodiments.

Referring now to FIG. 3A, a perspective view of the distal point 176 of the needle 172 is shown. FIG. 3A shows that the axial channel 182 runs from the beveled opening 178 in a longitudinal direction along the needle 172. The axial channel can be disposed along the needle 172 but does not enter the open bore 180 of the needle 172. FIG. 3B shows a cross-sectional view of the needle 172. Again, FIG. 3B illustrates that the axial channel 182 does not enter the open bore 180 of the needle 172. Although FIG. 3B shows axial channel 182 as comprising a rounded semi-circular cross-sectional shape, the axial channel 182 can comprise any suitable cross-sectional shape. For example, the axial channel 182 can comprise a square, rectangular, or other polygon cross-sectional shape.

In some embodiments, the axial channel 182 is configured to provide a primary indicator of blood flow or a primary "blood flash" to the medical practitioner when the needle 172 and catheter 115 have entered the vasculature (e.g., a vein) of the patient. When the medical practitioner has advanced the needle 172 and catheter 115 sufficiently and the needle 172 and catheter 115 have passed through a wall of a vein, blood is drawn along the axial channel 182 between the needle 172 and the catheter 115. This blood can then be seen by the medical practitioner through a translucent catheter 115. Upon seeing the blood drawn along the axial channel 182 or the primary blood flash, the medical practitioner knows that the catheter 115 has passed through the wall of the vein and that the catheter 115 is inserted into the vein. The medical practitioner can then retract the needle 172 and secure the catheter 115 in place. The primary blood flash can also indicate the medical practitioner that the vein has been accessed and that the needle 172 and/or catheter 115 do not need to be advanced further, thereby preventing the medical practitioner from advancing the needle 172 too far and traversing the vein. In some cases, the primary blood flash can be seen by the medical practitioner when the blood reaches the translucent chamber 126 of the catheter body 120.

In some embodiments, the catheter system 100 is configured to provide a secondary blood flash to the medical practitioner to confirm that the catheter 115 remains properly positioned within the vein during an extended phase of insertion by providing a continuous blood flash into the chamber 168. When the medical practitioner has advanced the needle 172 sufficiently and the needle 172 has entered the vein, blood can flow through the open bore 180 of the needle 172 into the chamber 168 of the needle hub body 156. With a translucent needle huh body 156, the chamber 168 can become a secondary flashback chamber and the visible presence of blood in this secondary flashback chamber can indicate to the medical practitioner that the needle 172 has entered the vein. The medical practitioner can then perform the extended phase of insertion by retracting the needle 172 while advancing the catheter 115 into position. During this extended phase of insertion, the medical practitioner can continuously observe the secondary flashback to be continuously reassured that the catheter 115 remains properly positioned within the vein (e.g., that the catheter 115 has not transfixed the vein and/or that clotting has not occurred). Once the catheter 115 is fully positioned, the medical practitioner can fully remove the needle 172 and secure the catheter 115 to the patient's skin.

Figure 3C:
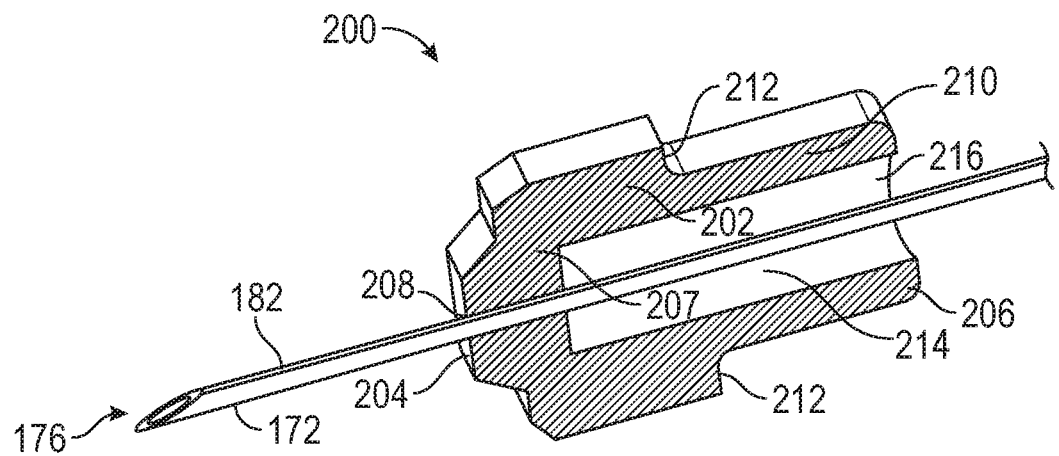
FIG. 3C is a cutaway view of a needle and a septum, according to some embodiments.
Figure 3D:
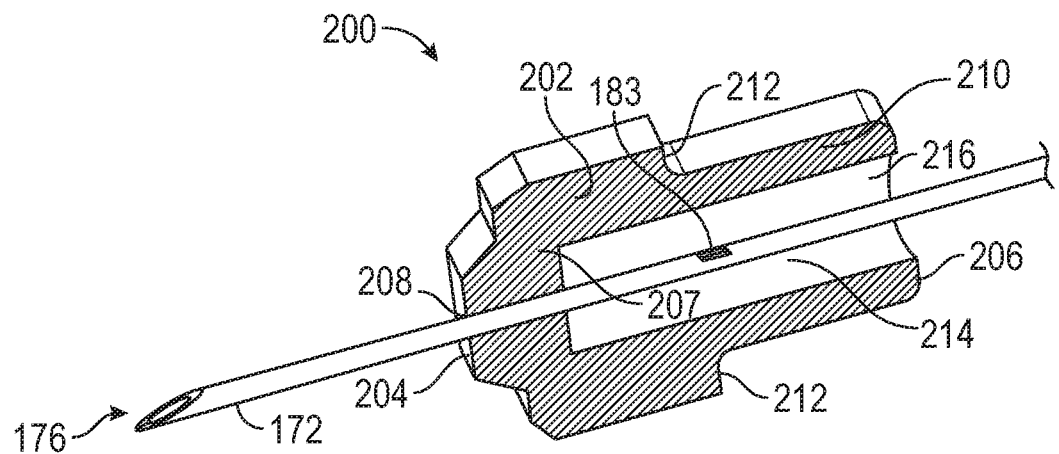
FIG. 3D is a cutaway view of a needle and a septum, according to some embodiments.

Referring now to FIGS. 3C and 3D, cutaway views of the septum 200 and the needle 172 are illustrated. FIG. 3C shows a cutaway view of the septum 200 as the needle 172 is being retracted. The septum 200 generally comprises a tubular and/or cylindrical shape. While the septum 200 can comprise any suitable component or configuration, at least in some cases, the septum 200 comprises a septum body 202 with a distal end 204 and a proximal end 206. In other cases, the septum 200 can comprise a distal wall 207 with a slit 208 therethrough. The slit 208 can be configured allow the needle 172 to pass therethrough while preventing passage of fluid through the slit 208. The septum 200 can also comprise an extension 210 extending from the septum body 202 at a shoulder 212. The septum body 202 and/or the extension 210 can define a lumen 214 with a proximal opening 216. FIG. 3C also shows the orientation of the axial channel 182 with respect to the septum 200 and the slit 208. In some cases, as the needle 172 is retracted, the axial channel 182 slidably passes through the slit 208. The slit 208 can be configured to conform to the axial channel 182 as it slidably passes through the slit 208, thereby excluding any fluid (e.g., blood) that may be in the axial channel 182. Thus, the slit 208 excludes any fluid that may be in the axial channel 182 and prevents the fluid from entering the lumen 214 of the septum 200.

FIG. 3D illustrates that one potential outcome of employing the notched opening 183 is leaking through the notched opening 183 into the lumen 214 of the septum 200 as the needle 172 is retracted. As the needle 172 is retracted, the notched opening 183 traverses the slit 208 and enters the lumen 214 of the septum 200. When the notched opening 183 is within the lumen 214 of the septum 200, fluid (e.g., blood) can pass through the open bore 180 of the needle 172 and enter into the lumen 214. The fluid can then leak from the lumen 214 into the proximal extension 130 and can then leak from the catheter system 100.

Another potential outcome of employing the notched opening 183 is flooding of the chamber 168 of the needle hub body 156 during pre-priming. This flooding of the chamber 168 can occur when the medical practitioner pre-primes the catheter system 100 with saline. During pre-priming of the catheter system 100, the medical practitioner infuses saline into the Y-port 128. The infused saline passes through the Y-port 128 and enters the chamber 126 of the catheter hub body 120 and can then pass into an interstitial space between an outer diameter of the needle 172 and an inner diameter of the catheter 115. The infused saline can flow through this interstitial space and can flow into the open bore 180 through the notched opening 183, Once in the open bore 180, the infused saline can flow into and "flood" the chamber 168 of the needle hub body. The flooded saline in the chamber 168 can often prevent an effective blood flashback in the chamber 168. Flooding of the chamber 168 when using a notched opening 183 can be more likely under certain conditions. For example, in some cases, when the distal end 116 of the catheter 115 is pointed vertically upwards during pre-priming, gravity can help draw the infused saline through the notched opening 183, down the open bore 180, and into the chamber 168. In other cases, larger gauges of catheter 115 and/or needle 172 can also lead to flooding of the chamber 168.

In some embodiments, when the needle 172 is configured with the axial channel 182 in place of the notched opening 183, independent fluid pathways are provided for each of the open bore 180 of the needle 172 and the axial channel 182 of the needle 172. For example, when the needle 172 is configured with the axial channel 182 in place of the notched opening 183, an independent fluid pathway can be provided along the open bore 180 from the distal point 176 to the proximal end 174 and opening into the chamber 168. Likewise, the axial channel 182 can provide an independent fluid pathway along the outer diameter of the needle 172 and into the chamber 126 of the catheter hub body 120. In each case, the independent fluid pathway within the open bore 180 of the needle 172 and the independent fluid pathway formed by the axial channel 182 can be fluidically isolated from each other and fluid flow between each of the independent fluid pathways can be prevented.

In some embodiments, when the needle 172 is configured with the axial channel 182 in place of the notched opening 183, the independent fluid pathway provided by the axial channel 182 avoids leakage of blood into the lumen 214 of the septum 200 as the needle 172 is retracted. When the axial channel 182 is employed instead of the notched opening 183, the needle 172 can be retracted without any leakage of blood into the lumen 214 because the independent fluid pathway provided by the axial channel 182 is fluidically isolated from the independent fluid pathway provided by the open bore 180. As the needle 172 is retracted, the axial channel 182 can slidably pass through the slit 208 with the slit 208 conforming to the axial channel 182 and excluding any blood that may be in the axial channel 182, thereby preventing any blood from entering the lumen 214 of the septum 200. Thus, a configuration comprising the axial channel 182 instead of the notched opening 183 can avoid leakage of blood into the lumen 214 and any further leakage of blood into the proximal extension 130.

In some embodiments, when the needle 172 is configured with the axial channel 182 in place of the notched opening 183, the independent fluid pathway provided by the axial channel 182 of the needle 172 avoids flooding of the chamber 168 during pre-priming with saline. For example, when the needle 172 is configured with the axial channel 182 in place of the notched opening 183, the medical practitioner can infuse saline through the Y-port 128 into the chamber 126 of the catheter hub body 120. The infused saline can then flow into the interstitial space between the outer diameter of the needle 172 and the inner diameter of the catheter 115. In some cases, the infused saline can also flow along the independent fluid pathway provided by the axial channel 182. Because the independent fluid pathway provided by the open bore 180 is fluidically isolated, infused saline from the pre-priming cannot enter the independent fluid pathway provided by the open bore 180 and flooding of the chamber 168 can be avoided. With this configuration, flooding of the chamber 168 can also be avoided when the distal end 116 of the catheter 115 is pointed vertically upwards during pre-priming and when larger gauges of catheter 115 and/or needle 172 are used.

Figure 4:
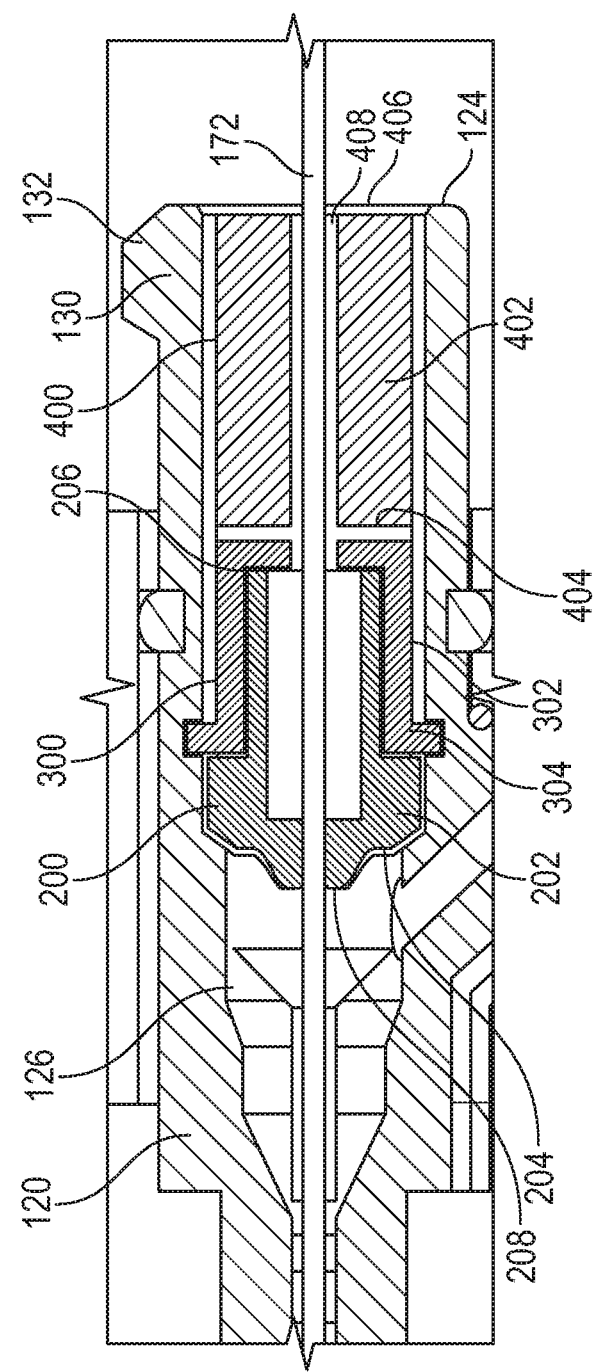
FIG. 4 is a cutaway view of a catheter hub body, according to some embodiments.

Referring now to FIG. 4, a cutaway view of the catheter hub body 120 in the insertion configuration with the needle 172 in place is illustrated. FIG. 4 shows that the septum 200 can fit within the catheter hub body 120 to define the chamber 126 of the catheter hub body 120. The distal wall 207 of the septum 200 can seal the chamber 126 to prevent fluid from leaking past the septum 200. The slit 208 can also be configured to prevent fluid from leaking past the septum 200 when the needle 172 is in place within the slit 208 and when the needle 172 is removed from the slit 208. The septum canister 300 can be configured to secure the septum 200 within the catheter hub body 120. The septum canister 300 can also be configured to secure the septum 200 within the catheter hub body 120 to prevent fluid from leaking past the septum 200. The septum canister 300 can comprise a body 302 with a distal end 304 and a proximal end 306. In some cases, the septum canister 300 can comprise a wall 307. The septum canister 300 can also comprise a septum canister opening 308 configured to permit the needle 172 to pass therethrough. In other cases, the septum canister 300 can comprise a distal extension 310 extending distally from the wall 307. The distal extension 310 can define a first lumen 312. In yet other cases, the septum 300 can comprise a retaining ridge 314 configured to retain the septum 300 within the catheter hub body 120.

In some embodiments, the needle safety 400 is disposed within the catheter hub body 120 proximal to the septum canister 300. The needle safety 400 can comprise a body 402 with a distal end 404 and a proximal end 406. The needle safety 400 can also comprise a central passageway 408. As described below, the needle safety 400 can protect the medical practitioner from an inadvertent needle stick by engaging the distal point 176 of the needle 172. The engaged needle safety 400 is retained on the distal point 176 of the needle 172 as the needle safety 400 is removably disengaged from the catheter adapt 102 (See FIG. 6).

Figure 5A:
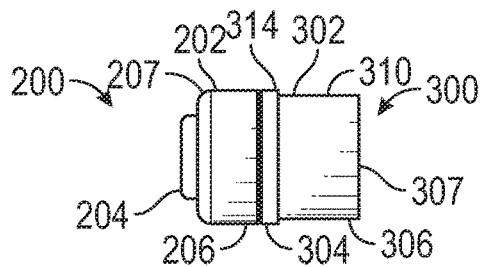
FIG. 5A is a side view of a septum and a septum canister, according to some embodiments.
Figure 5B:
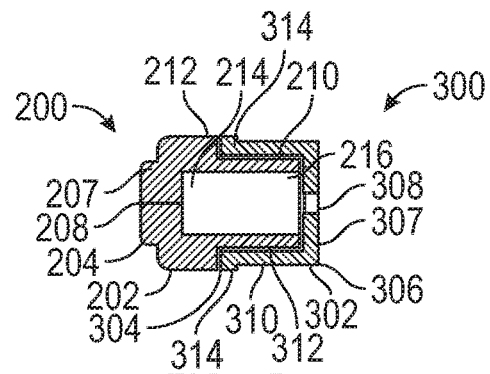
FIG. 5B is a cutaway view of a septum and a septum canister, according to some embodiments.

Referring now to FIGS. 5A to 5H, some embodiments of various configurations of the septum 200 and the septum canister 300 are illustrated. FIG. 5A illustrates a side view of the septum 200 and the septum canister 300 and FIG. 5B illustrates a cut-away view of FIG. 5A. FIGS. 5A and 5B illustrate that the septum 200 can comprise the generally tubular and/or cylindrically-shaped septum body 202 that includes the distal end 204 and the proximal end 206. The septum body 202 can comprise the distal wall 207 with the slit 208 therethrough. The septum body 202 can also comprise an extension 210 extending from the septum body 202 at the shoulder 212. The septum body 202 and/or the extension 210 can define the lumen 214 with the proximal opening 216.

The septum canister 300 can comprise the generally tubular and/or cylindrically-shaped body 302 with the distal end 304 and the proximal end 306. The septum canister 300 can comprise the wall 307 and the septum canister opening 308 in the wall 307. The septum canister 300 can comprise the distal extension 310 extending distally from the all 307 and defining the first lumen 312. The retaining ridge 314 can be disposed on a distal end of the distal extension 310. In some cases, the extension 210 of the septum body 202 can be configured to be slidably received within the first lumen 312 of the septum canister 300. In other cases, the retaining ridge 314 of the septum canister 300 can fit against the shoulder 212 of the septum 200.

Figure 5C:
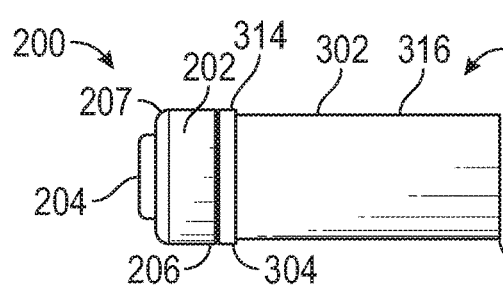
FIG. 5C is a side view of a septum and a septum canister, according to some embodiments.
Figure 5D:
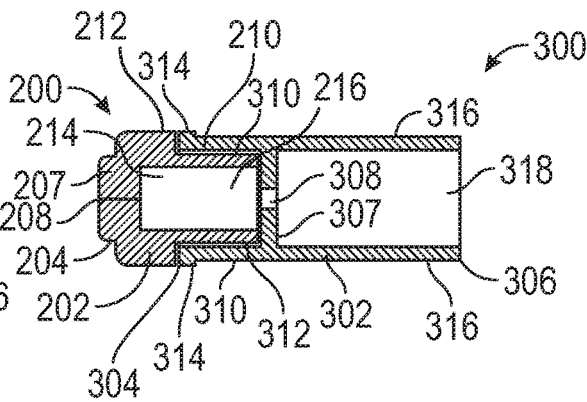
FIG. 5D is a cutaway view of a septum and a septum canister, according to some embodiments.

Referring now to FIGS. 5C and 5D, some embodiments of various configurations of the septum 200 and the septum canister 300 are illustrated. FIG. 5C illustrates a side view of the septum 200 and the septum canister 300 and FIG. 5D illustrates a cut-away view of FIG. 5C. FIGS. 5C and 5D illustrate that the septum 200 can comprise the generally tubular and/or cylindrically-shaped septum body 202 that includes the distal end 204 and the proximal end 206. The septum body 202 can comprise the distal wall 207 with the slit 208 therethrough. The septum body 202 can also comprise an extension 210 extending from the septum body 202 at the shoulder 212. The septum body 202 and/or the extension 210 can define the lumen 214 with the proximal opening 216.

The septum canister 300 can comprise the generally tubular and/or cylindrically-shaped body 302 with the distal end 304 and the proximal end 306. The septum canister 300 can comprise the wall 307 and the septum canister opening 308 in the wall 307. The septum canister 300 can comprise the distal extension 310 extending distally from the wall 307 and defining the first lumen 312. The retaining ridge 314 can be disposed on a distal end of the distal extension 310. The extension 210 of the septum body 202 can be configured to be slidably received within the first lumen 312 of the septum canister 300 and the retaining ridge 314 of the septum canister 300 can fit against the shoulder 212 of the septum 200.

In some instances, the septum canister 300 can comprise a proximal extension 316 extending from the wall 307. The proximal extension 316 of the septum canister 300 can define a second lumen 318. In other instances, the proximal extension 316 of the septum canister 300 can be configured to extend into the proximal extension 130 of the catheter hub body 120. In yet other instances, the second lumen 318 can be configured to selectively and removably receive at least a portion of the needle safety 400.

Figure 5E:
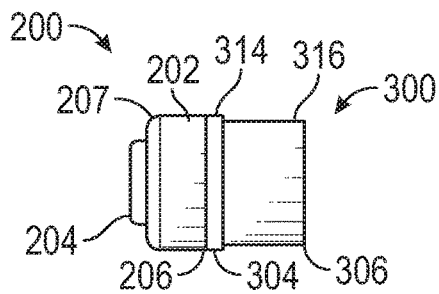
FIG. 5E is a side view of a septum canister, according to some embodiments.
Figure 5F:
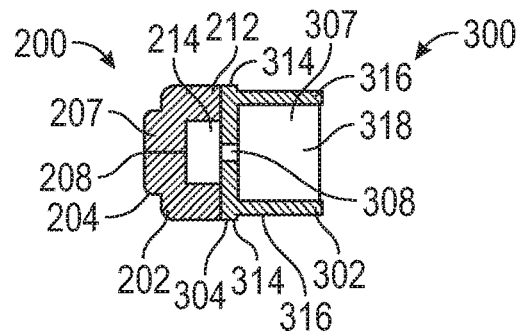
FIG. 5F is a cutaway view of a septum and a septum canister, according to some embodiments.

Referring now to FIGS. 5E and 5F, some embodiments of various configurations of the septum 200 and the septum canister 300 are illustrated. FIG. 5E illustrates a side view of the septum 200 and the septum canister 300 and FIG. 5F illustrates a cut-away view of FIG. 5E. FIGS. 5E and 5F illustrate that the septum 200 can comprise a generally disc-shaped septum body 202 that includes the distal end 204 and the proximal end 206 and defines the lumen 214. The septum body 202 can comprise the slit 208. The septum canister 300 can comprise the generally tubular and/or cylindrically-shaped body 302 with the distal end 304 and the proximal end 306.

The septum canister 300 can comprise the wall 307 and the septum canister opening 308 in the wall 307. The septum canister 300 can comprise the proximal extension 316 extending proximally from the wall 307 and defining the second lumen 318. The proximal extension 316 of the septum canister 300 can be configured to extend into the proximal extension 130 of the catheter hub body 120. The second lumen 318 can also be configured to selectively and removably receive at least a portion of the needle safety 400. In some cases, the retaining ridge 314 can extend outward from the wall 307. In other cases, the retaining ridge 314 of the septum canister 300 can fit against the shoulder 212 of the septum 200.

Figure 5G:
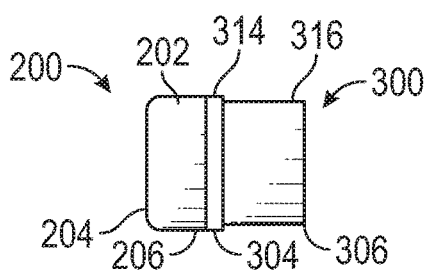
FIG. 5G is a side view of a septum and a septum canister, according to some embodiments.
Figure 5H:
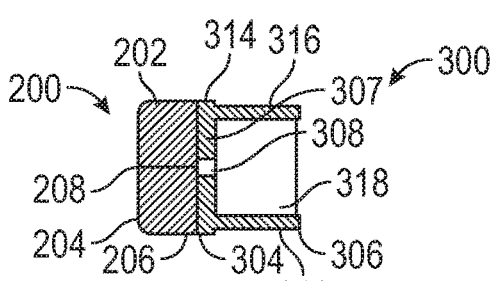
FIG. 5H is a cutaway tie of a septum and a septum canister, according to some embodiments.

Referring now to FIGS. 5G and 5H, some embodiments of various configurations of the septum 200 and the septum canister 300 are illustrated. FIG. 5G illustrates a side view of a septum 200 and a septum canister 300 and FIG. 5H illustrates a cut-away view of FIG. 5G. FIGS. 5G and 5H illustrate that the septum 200 can comprise a generally solid disc-shaped septum body 202 that includes the distal end 204 and the proximal end 206. The septum body 202 can comprise the slit 208 therethrough.

The septum canister 300 can comprise the generally tubular and/or cylindrically-shaped body 302 with the distal end 304 and the proximal end 306. The septum canister 300 can comprise the wall 307 and the septum canister opening 308 in the wall 307. The septum canister 300 can comprise the proximal extension 316 extending proximally from the wall 307 and defining the second lumen 318. The proximal extension 316 of the septum canister 300 can be configured to extend into the proximal extension 130 of the catheter hub body 120. The second lumen 318 can also be configured to selectively and removably receive at least a portion of the needle safety 400. The retaining ridge 314 can extend outward from the wall 307. In some cases, a distal side of the wall 307 can fit against the proximal end 206 of the septum 200.

Figure 6:
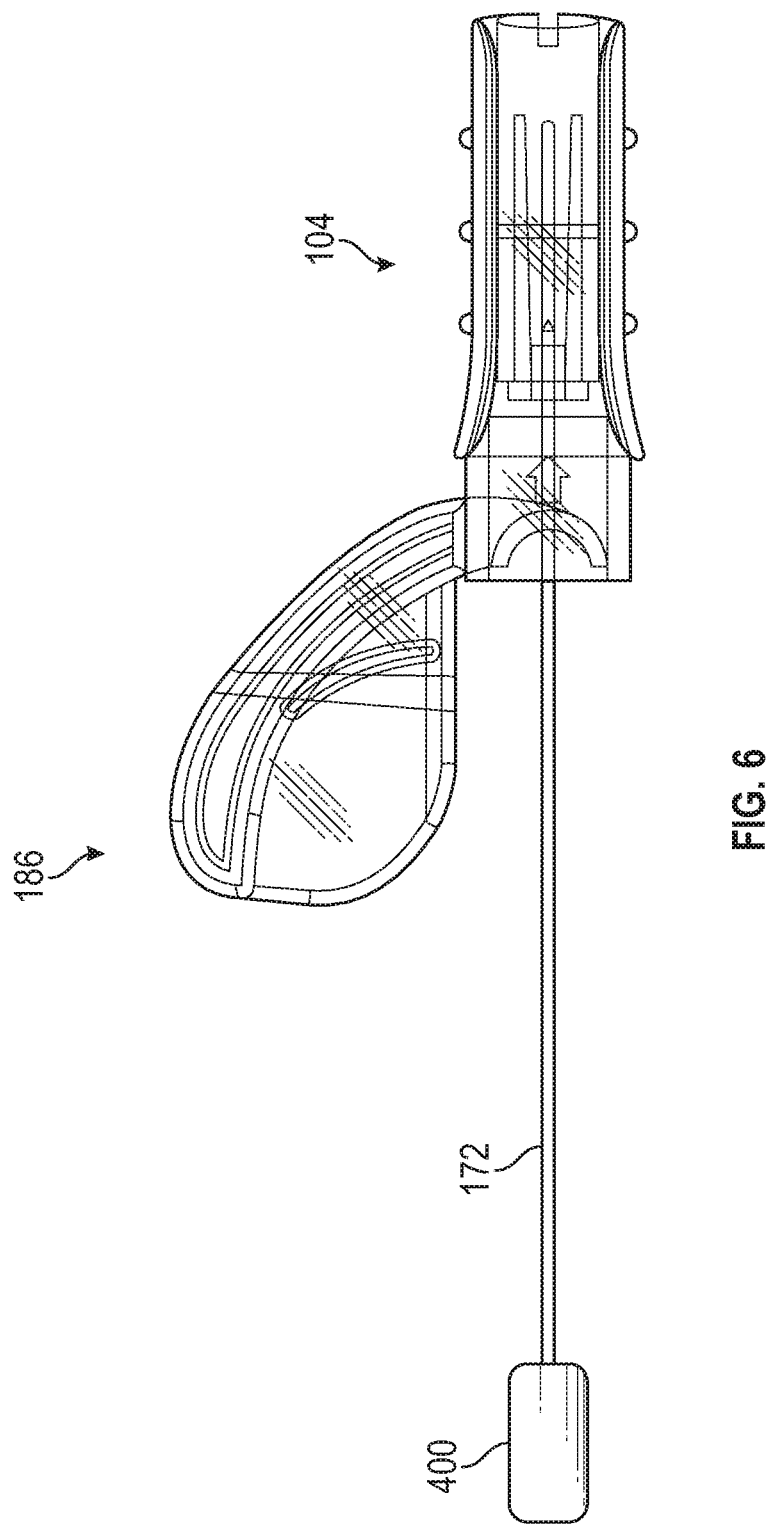
FIG. 6 is a side view of a needle hub and a needle safety, according to some embodiments.

Referring now to FIG. 6, a side view of the needle hub 104 in a separated configuration is illustrated. FIG. 6 shows that in the separated configuration the needle hub 104 can be completely retracted and separated from the catheter adapter 102. The first wing 146 is also separated from the paddle grip 186. In the separated configuration the needle 172 can be completely removed from the catheter adapter 102. Likewise, the engaged needle safety 400 is removably disengaged from the catheter adapter 102 and the engaged needle safety 400 is retained on the distal point 176 of the needle 172 to protect the medical practitioner from an inadvertent needle stick. The separated needle hub 104 can then be disposed of properly.

In some embodiments, the catheter system 100, such as, for example, the catheter system 100 described in any of the FIGS. 1-6, may include a needle safety 400. The needle safety 400 may include any safety mechanism configured to secure the distal point 176 and/or beveled opening 178 of the needle 172 when the needle 172 is withdrawn from the catheter 115 of the catheter system 100, preventing accidental needle sticks.

The needle safety 400 may be coupled with the catheter system 100 in any number of ways. In some embodiments, the needle safety 400 may include an internal interlock in which the needle safety 400 is coupled with an internal surface of the catheter adapter 102. Coupling may include threading, fitting, snapping, connecting, attaching, fastening, clipping, hooking, or any other suitable cans of coupling. Non-limiting examples of the needle safety 400 that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; and U.S. Patent Application No. 62/314,262, titled CANNULA CAPTURE MECHANISM, filed Mar. 28, 2016, each of which is herein incorporated by reference in its entirety. In some embodiments, the needle safety 400 may include a clip disposed within the catheter adapter 102, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the needle safety 400 may include an external interlock in which the needle safety 400 is coupled with an external surface of the catheter adapter 102. In some embodiments, the needle safety 400 may be coupled with an external surface of the catheter adapter 102 and an internal and/or external surface of the needle hub 104. Coupling may include threading, fitting, snapping, connecting, attaching, fastening, clipping, hooking, or any other suitable means of coupling. Non-limiting examples of the needle safety 400 that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the needle safety 400 may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. The V-clip may also selectively retain a portion of the catheter adapter 102.

In some embodiments, a defeatable mechanical connection is provided between the needle safety 400 and at least one other component of the catheter system 100. In some instances, the mechanical connection is defeated upon securement of the distal point 176 of the needle 172 within the needle safety 400. In some embodiments, a surface of the needle safety 400 is selectively coupled to one or more of the following: the catheter adapter 102, the needle hub 104, the stabilization platform 118, the proximal extension 130, the paddle grip 186, and the septum canister 300.

In some embodiments, the needle safety 400 may include a safety barrel, which may be spring-loaded. For example, the safety barrel may be spring loaded as in the BD™ Insyte® Autoguard™ BC shielded protective IV catheter. In some embodiments, the needle safety 400 may be passively and/or actively activated. In some embodiments, the needle safety 400 may be configured to interact with a needle feature, such as a ferrule, notch, crimp or bump on the needle 172. In some embodiments, the needle safety 400 may include an arm or lever that may be actuated to capture the distal point 176 within the needle safety 400 and prevent the distal point 176 from emerging prior to safe disposal. In some embodiments, the needle safety 400 may be attached to a body of the needle 172 and may be capable of sliding along the length thereof.

In some embodiments, in an insertion configuration prior to catheterization, the needle safety 400 may be disposed between the catheter adapter 102 and the needle hub 104. In some embodiments, the catheter adapter 102 and the needle hub 104 may be spaced apart by at least a portion of the needle safety 400 in the insertion configuration prior to catheterization. In some embodiments, in the insertion configuration prior to catheterization, a proximal end of the catheter adapter 102 may be disposed between the distal end 404 of the needle safety 400 and a distal end of a grip of the needle hub 104, such as, for example, a paddle grip 186. In some embodiments, in the insertion configuration prior to catheterization, the proximal end 124 of the catheter hub body 120 may be disposed between the distal end 404 of the needle safety 400 and the proximal end 124 of a grip of the needle hub 104. In some embodiments, a portion of the needle safety may overlap with a portion of the grip of the needle hub 104. In some embodiments, at least a portion of at least one of the catheter adapter 102 and the grip overlaps at least some portion of the needle safety 400. In some embodiments, no portion of the catheter hub body 120 or the grip overlaps any portion of the needle safety 400.

Figure 7A:
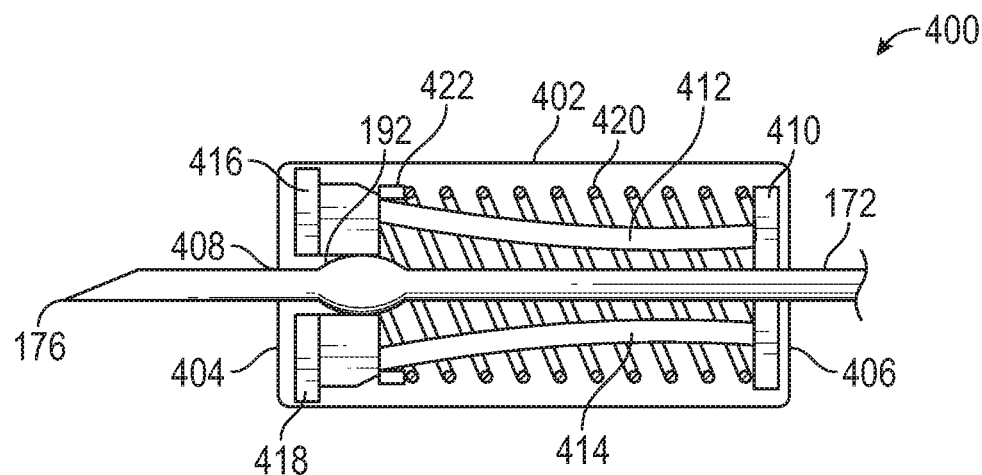
FIG. 7A is a cutaway view of a needle and a needle safety as the needle is retracting, according to some embodiments.
Figure 7B:
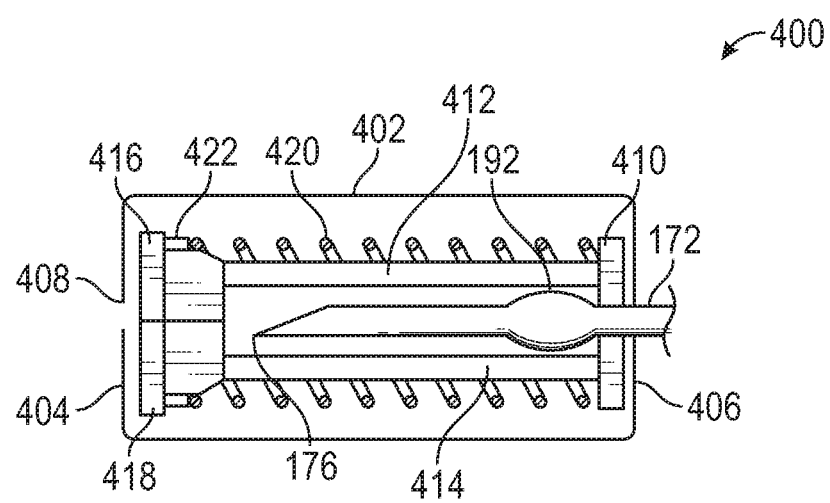
FIG. 7B is a cutaway view of a needle and a needle safety with the needle retracted, according to some embodiments.

Referring now to FIGS. 7A to 7B, some embodiments of the needle safety 400 similar to embodiments disclosed in U.S. Patent Application No. 62/314,262, titled CANNULA CAPTURE MECHANISM, filed Mar. 28, 2016 are illustrated. FIG. 7A shows embodiments of the needle safety 400 as the distal point 176 of needle 172 is retracted into the needle safety 400. FIG. 7B shows embodiments of the needle safety 400 with the distal point 176 of the needle engaged in the needle safety 400. In some cases, the needle safety 400 comprises the body 402 with a distal end 404, a proximal end 406, and the central passageway 408 therethrough. The needle safety 400 can comprise a base 410 attached to a first splayed member 412 and a second splayed member 414. The first splayed member 412 can comprise a first end piece 416. The second splayed member 414 can comprise a second end piece 418. The needle safety 400 can also comprise a spring 420 configured to bias a retaining ring 422 against the first end piece 416 and the second end piece 418, thereby biasing the first end piece 416 against the second end piece 418.

As shown in FIG. 7A, as the needle 172 is retracted, the needle 172 is able to slidably translate between the first and second end pieces 416, 418. The needle 172 can comprise a needle feature such as a protuberance 192 near the distal point 176 of the needle 172. As the protuberance 192 is drawn through the first and second end pieces 416, 418, the first and second end pieces 416, 418 are biased open and the protuberance 192 is able to pass between first and second end pieces 416, 418. As shown in FIG. 7B, once the distal point 176 has passed between the first and second end pieces 416, 418, the first and second end pieces 416, 418 are biased together preventing the distal point 176 of the needle 172 from emerging from the needle safety 400. The protuberance 192 can prevent the needle 172 from continuing to pass through the needle safety 400, effectively irreversibly engaging the needle safety 400 on the distal point 176 to prevent an inadvertent needle stick.

Figure 8A:
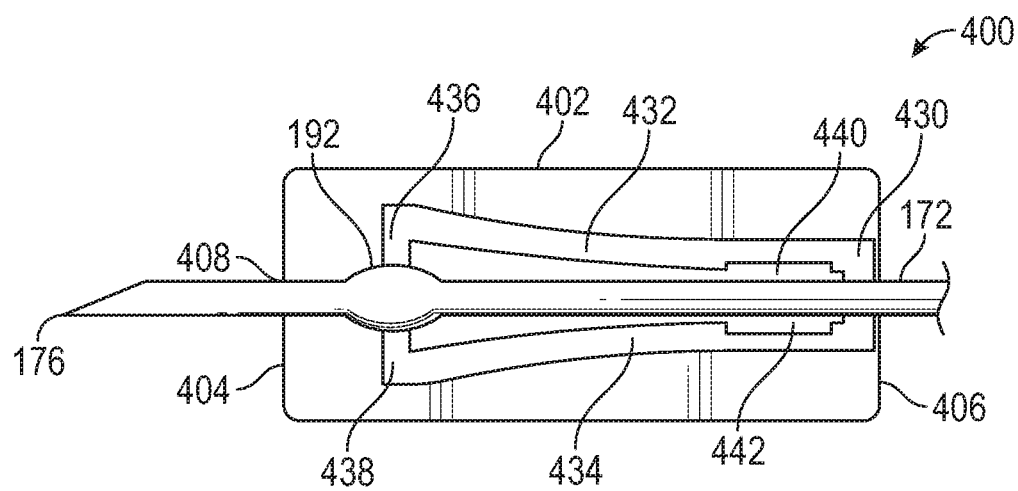
FIG. 8A is a cutaway view of a needle and a needle safety as the needle is retracting, according to some embodiments.
Figure 8B:
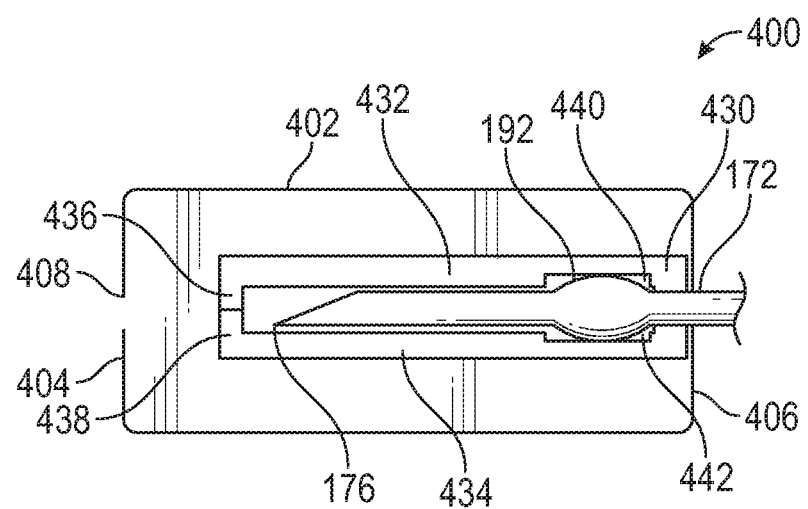
FIG. 8B is a cutaway view of a needle and a needle safety with the needle retracted, according to some embodiments.

Referring now to FIGS. 8A to 8B, some embodiments of the needle safety 400 similar to embodiments disclosed in U.S. Patent Application No. 62/314,262, titled CANNULA CAPTURE MECHANISM, filed Mar. 28, 2016 are illustrated. FIG. 8A shows embodiments of the needle safety 400 as the distal point 176 of needle 172 is retracted into the needle safety 400. FIG. 8B shows embodiments of the needle safety 400 with the distal point 176 of the needle engaged in the needle safety 400. In some cases, the needle safety 400 comprises the body 402 with a distal end 404, a proximal end 406, and the central passageway 408 therethrough. The needle safety 400 can comprise a base 430 attached to a first splayed member 432 and a second splayed member 434. The first splayed member 432 can comprise a first end piece 436. The second splayed member 434 can comprise a second end piece 438. The first splayed member 432 can comprise a first cutout 440. The second splayed member 434 can comprise a second cutout 442. The first and second cutouts 440, 442 can be sized to receive the protuberance 192 of the needle 172. The first splayed member 432 and the second splayed member 434 bias the first end piece 436 and the second end piece 438 together.

As shown in FIG. 8A, as the needle 172 is retracted, the needle 172 is able to slidably translate between the first and second end pieces 436, 438. The needle 172 can comprise the protuberance 192 near the distal point 176 of the needle 172. As the protuberance 192 is drawn through the first and second end pieces 436, 438, the first and second end pieces 416, 418 are biased open by the protuberance 192 and the protuberance 192 is able to pass between first and second end pieces 436, 438. As shown in FIG. 7B, once the distal point 176 has passed between the first and second end pieces 436, 438, the first and second end pieces 436, 438 are biased together preventing the distal point 176 of the needle 172 from emerging from the needle safety 400. The protuberance 192 can be received by the first and second cutouts 440, 442 effectively engaging the protuberance 192 and effectively irreversibly engaging the needle safety 400 on the distal point 176 to prevent an inadvertent needle stick.

Figure 9A:
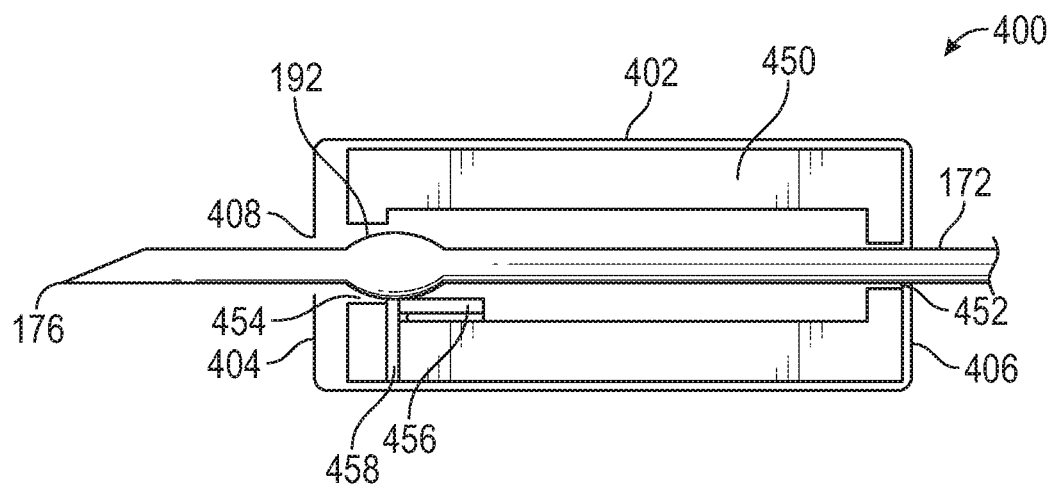
FIG. 9A is a cutaway view of a needle and a needle safety as the needle is retracting, according to some embodiments.
Figure 9B:
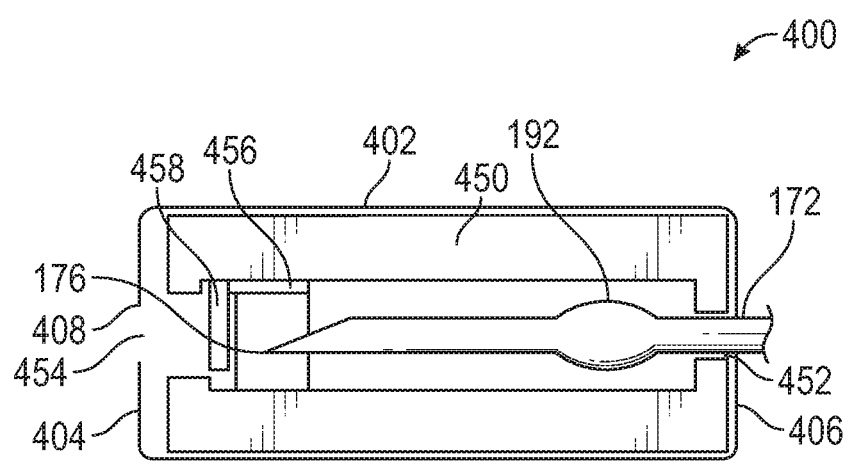
FIG. 9B is a cutaway view of a needle and a needle safety with the needle retracted, according to some embodiments.

Referring now to FIGS. 9A to 9B, some embodiments of the needle safety 400 with a V-spring are illustrated. FIG. 9A shows embodiments of the needle safety 400 as the distal point 176 of needle 172 is retracted into the needle safety 400. FIG. 9B shows embodiments of the needle safety 400 with the distal point 176 of the needle engaged in the needle safety 400. In some cases, the needle safety 400 comprises the body 402 with a distal end 404, a proximal end 406, and the central passageway 408 therethrough. The needle safety 400 can comprise a spring frame 450 with a proximal opening 452 and a distal opening 454. The spring frame 450 can comprise a V-spring 456 with a shutter 458. The V-spring 456 can be configured to bias against the needle 172. As shown in FIG. 9A, as the needle 172 is retracted, the needle 172 is able to slidably translate between the distal opening 454 and the proximal opening 452, The needle 172 can comprise the protuberance 192 near the distal point 176 of the needle 172, As the needle 172 is drawn between the distal opening 454 and the proximal opening 452, the needle 172 and/or the protuberance 192 maintains the NT-spring 456 in a biased position against the spring frame 450

As shown in FIG. 9B, once the distal point 176 has cleared the V-spring 456, the V-spring 456 opens and the shutter 458 blocks the distal opening 454, thereby preventing the distal point 176 of the needle 172 from reemerging from the needle safety 400. The protuberance 192 can be retained by the proximal opening 452 effectively engaging the protuberance 192 and effectively irreversibly engaging the needle safety 400 on the distal point 176 to prevent an inadvertent needle stick.

Although the catheter system 100 can be manufactured from any suitable materials, at least in some embodiments, the catheter adapter 102 and the needle hub 104, are formed from thermoplastic polymeric resins such as polycarbonate, polystyrene, polypropylene, and other similar materials. The catheter adapter 102 and the needle hub 104 can be formed from a substantially transparent material to allow the medical practitioner to visibly ascertain the needle 172 as it is slidably removed and to view the primary and/or secondary blood flashback. The catheter 115 can be formed from thermoplastic resins such as polytetrafluoroethylene (PTFE), polyurethane, and other similar materials. In some cases, the catheter 115 can be formed from thermoplastic hydrophilic polyurethane that softens with exposure to physiological conditions within the patient's body. The needle 172, the spring 420, and the V-spring 456 can be formed from a stainless steel alloy or other similar material.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter system comprising:
   a catheter adapter comprising:
      a catheter hub comprising a distal end and a proximal end and defining a chamber extending between the distal end and the proximal end;
      a catheter extending from the distal end of the catheter hub and in fluid communication with the chamber;
      a stabilization platform;
      a septum disposed within the chamber, wherein the septum comprises a distal wall, a proximal opening, a shoulder disposed between the distal wall and the proximal opening, a first extension extending proximally from the shoulder, and a first lumen extending from the distal wall through the proximal opening; and
      a septum canister, comprising a wall, a second extension extending distally from the wall, a third extension extending proximally from the wall, and a wall opening in the wall, wherein the second extension defines a second lumen, wherein the third extension defines a third lumen, wherein the first extension is slidably received within the second lumen, wherein the shoulder abuts the second extension; and
   a needle hub comprising:
      a needle configured to slidably fit within the catheter, wherein the wall opening is configured to receive the needle;
      a needle hub body anchored to a proximal end of the needle,
   wherein in an insertion configuration, the proximal end of the catheter hub is removably coupled within a distal opening of the needle hub, and
   wherein after placement of the catheter, the needle hub is retracted from the catheter adapter to slidably remove the needle from the catheter and to separate the needle hub from the catheter adapter.

2. The catheter system of claim 1, wherein the needle comprises an open bore in fluid communication with a chamber of the needle hub and wherein blood flows through the open bore to the chamber of the needle hub to provide a secondary blood flashback that indicates that the needle has entered a vasculature of a patient.

3. The catheter system of claim 1, wherein the stabilization platform further comprises a first wing comprising a generally planar shape to stably maintain the catheter adapter against a skin of a patient.

4. The catheter system of claim 1, wherein the stabilization platform further comprises a soft push tab configured to provide a grasping surface to manipulate and advance the catheter adapter.

5. The catheter system of claim 1, wherein the catheter hub further comprises a Y-port in fluid communication with the chamber of the catheter hub.

6. The catheter system of claim 1, wherein the needle hub further comprises a paddle grip extending from a distal end of the needle hub and configured to provide a grip surface to manipulate the needle hub.

7. The catheter system of claim 1, further comprising a needle safety configured protect against needle sticks by engaging a distal point of the needle as the needle is retracted from the catheter adapter.

8. A method of catheterization comprising:
   providing a catheter system comprising:
      a catheter adapter comprising:
         a catheter hub defining a chamber extending between a distal end and a proximal end;
         a catheter extending from the distal end of the catheter hub and in fluid communication with the chamber; and
         a stabilization platform;
         a septum disposed within the chamber, wherein the septum comprises a distal wall, a proximal opening, a shoulder disposed between the distal wall and the proximal opening, a first extension extending proximally from the shoulder, and a first lumen extending from the distal wall through the proximal opening; and a septum canister, comprising a wall, a second extension extending distally from the wall, a third extension extending proximally from the wall, and a wall opening in the wall, wherein the second extension defines a second lumen, wherein the third extension defines a third lumen, wherein the first extension is slidably received within the second lumen, wherein the shoulder abuts the second extension; and a needle hub comprising a needle configured to slidably fit within the catheter and a needle hub body anchored to a proximal end of the needle, wherein the wall opening is configured to receive the needle;

inserting the needle and catheter at a catheter insertion site;

advancing the needle and catheter at the catheter insertion site until a primary blood flashback is provided in the chamber of the catheter hub;

securing the catheter at the catheter insertion site; and retracting the needle hub from the catheter adapter to slidably remove the needle from the catheter and to separate the needle hub from the catheter adapter.

9. The method of claim 8, further comprising, advancing the needle and catheter at the catheter insertion site until a secondary blood flashback is provided in a chamber of the needle hub.

10. The method of claim 8, wherein securing the catheter further comprises securing the stabilization platform against skin proximate to the catheter insertion site.

11. The method of claim 8, further comprising engaging a needle safety on a distal point of the needle as the needle is retracted from the catheter adapter.

12. A catheter system comprising:
a catheter adapter comprising:
    a catheter hub defining a chamber extending between a distal end and a proximal end of the catheter hub;
    a catheter extending from the distal end of the catheter hub and in fluid communication with the chamber;
    a stabilization platform comprising a first wing and a soft push tab;
    a septum disposed within the chamber, wherein the septum comprises a distal wall, a proximal opening, and a first lumen extending from the distal wall through the proximal opening; and
    a septum canister, comprising a wall, a proximal extension extending proximally from the wall and defining a second lumen, a wall opening in the wall, and a retaining ridge aligned with the wall and extending outwardly from the wall, wherein the wall forms a distal-most end of the septum canister, wherein the septum abuts the wall; and
a needle hub comprising a needle configured to slidably fit within the catheter and a needle hub body anchored to a proximal end of the needle, wherein the wall opening is configured to receive the needle;
wherein in an insertion configuration, a proximal extension of the catheter hub is removably coupled within a distal opening of the needle hub, and
wherein after placement of the catheter, the needle hub is retracted from the catheter adapter to slidably remove the needle from the catheter and to separate the needle hub from the catheter adapter.

13. The catheter system of claim 12, wherein blood flows through an open bore of the needle to the chamber of the needle hub to provide a secondary blood flashback to indicate that the needle has entered a vasculature of a patient.

14. The catheter system of claim 12, further comprising a needle safety removably disposed within the proximal extension of the catheter hub and configured protect against needle sticks by engaging a distal point of the needle as the needle is retracted from the catheter adapter.

* * * * *